United States Patent
Kopelman

(10) Patent No.: US 10,610,107 B2
(45) Date of Patent: Apr. 7, 2020

(54) METHODS AND SYSTEMS FOR CREATING AND INTERACTING WITH THREE DIMENSIONAL VIRTUAL MODELS

(71) Applicant: Align Technology, Inc., San Jose, CA (US)

(72) Inventor: Avi Kopelman, Palo Alto, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 16/176,474

(22) Filed: Oct. 31, 2018

(65) Prior Publication Data
US 2019/0167113 A1    Jun. 6, 2019

Related U.S. Application Data

(63) Continuation of application No. 15/050,673, filed on Feb. 23, 2016, which is a continuation of application (Continued)

(51) Int. Cl.
*G06T 19/20* (2011.01)
*A61C 7/00* (2006.01)
(Continued)

(52) U.S. Cl.
CPC .......... *A61B 5/0088* (2013.01); *A61B 5/0062* (2013.01); *A61B 5/4547* (2013.01); *A61C 5/77* (2017.02); *A61C 7/002* (2013.01); *A61C 9/0053* (2013.01); *A61C 13/0004* (2013.01); *G06F 17/50* (2013.01); *G06T 7/0012* (2013.01);
(Continued)

(58) Field of Classification Search
None
See application file for complete search history.

(56) References Cited

U.S. PATENT DOCUMENTS 2,467,432 A    4/1949  Kesling
3,407,500 A   10/1968  Kesling
(Continued)

FOREIGN PATENT DOCUMENTS

AU    3031677 A    5/1979
AU     517102 B2    7/1981
(Continued)

OTHER PUBLICATIONS

Co-pending U.S. Appl. No. 16/586,528, filed Sep. 27, 2019.
(Continued)

*Primary Examiner* — Bijan Mapar
(74) *Attorney, Agent, or Firm* — Wilson Sonsini Goodrich & Rosati

(57) ABSTRACT

Systems and methods are provided for preparation of orthodontics and prosthodontics. A method may include scanning a patient's teeth to form first 3D data of the patient's teeth including a removable element that obscures part of the dental surfaces of the patient's teeth and non-obscured tooth surfaces, removing the removable element form the patient's teeth so that the removable element no longer obscures the part of the dental surfaces of the patient's teeth, and scanning the previously obscured part of the dental surfaces of the patent's teeth and the non-obscured tooth surfaces.

30 Claims, 8 Drawing Sheets

Related U.S. Application Data

No. 13/574,723, filed as application No. PCT/IL2011/000574 on Jul. 19, 2011, now Pat. No. 9,299,192.

(60) Provisional application No. 61/365,556, filed on Jul. 19, 2010.

(51) Int. Cl.

| | | |
|---|---|---|
| *G06T 19/00* | (2011.01) | |
| *G06F 17/50* | (2006.01) | |
| *G06T 7/00* | (2017.01) | |
| *A61B 5/00* | (2006.01) | |
| *A61C 5/77* | (2017.01) | |
| *A61C 13/00* | (2006.01) | |
| *A61C 9/00* | (2006.01) | |
| *B33Y 80/00* | (2015.01) | |
| *G16H 20/40* | (2018.01) | |
| *A61B 1/00* | (2006.01) | |
| *A61C 19/04* | (2006.01) | |

(52) U.S. Cl.
CPC ............... *G06T 19/00* (2013.01); *G06T 19/20* (2013.01); *A61B 1/00039* (2013.01); *A61B 1/00172* (2013.01); *A61C 19/04* (2013.01); *B33Y 80/00* (2014.12); *G06T 2200/04* (2013.01); *G06T 2207/30036* (2013.01); *G06T 2210/41* (2013.01); *G06T 2219/2004* (2013.01); *G06T 2219/2021* (2013.01); *G16H 20/40* (2018.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |

(56) References Cited

U.S. PATENT DOCUMENTS

| | | |
|---|---|---|
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,227,850 B1 | 5/2001 | Chishti et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,334,853 B1 | 1/2002 | Kopelman et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,739,869 B1 | 5/2004 | Taub et al. |
| 7,029,275 B2 | 4/2006 | Rubbert et al. |
| 7,347,686 B2 | 3/2008 | Marshall et al. |
| 7,476,100 B2 | 1/2009 | Kuo et al. |
| 7,536,234 B2 | 5/2009 | Kopelman et al. |
| 7,555,403 B2 | 6/2009 | Kopelman et al. |
| 9,299,192 B2 | 3/2016 | Kopelman |
| 2002/0006217 A1* | 1/2002 | Rubbert ............... A61C 7/00 382/131 |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0215764 A1 | 11/2003 | Kopelman et al. |
| 2003/0224311 A1 | 12/2003 | Cronauer |
| 2003/0232302 A1 | 12/2003 | Babayoff et al. |
| 2004/0128010 A1 | 7/2004 | Pavlovskaia et al. |
| 2005/0055118 A1 | 3/2005 | Nikolskiy et al. |
| 2005/0283065 A1* | 12/2005 | Babayoff ........... A61B 1/00009 600/407 |
| 2007/0015111 A1 | 1/2007 | Kopelman et al. |
| 2007/0172112 A1* | 7/2007 | Paley ................ A61B 5/4547 382/154 |
| 2007/0236494 A1* | 10/2007 | Kriveshko ......... A61C 13/0004 345/419 |
| 2008/0206705 A1 | 8/2008 | Kaza et al. |
| 2009/0316966 A1 | 12/2009 | Marshall et al. |
| 2010/0114351 A1 | 5/2010 | Kopelman et al. |
| 2013/0110469 A1 | 5/2013 | Kopelman |
| 2016/0171128 A1 | 6/2016 | Kopelman |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1901235 A1 | 3/2008 |
| ES | 463897 A1 | 1/1980 |
| FR | 2369828 A1 | 6/1978 |
| FR | 2652256 A1 | 3/1991 |
| GB | 1550777 A | 8/1979 |
| JP | S53588191 A | 5/1978 |
| JP | H0428359 A | 1/1992 |
| JP | 08508174 | 9/1996 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |
| WO | WO-03094102 A1 | 11/2003 |
| WO | WO-2004087000 A1 | 10/2004 |
| WO | WO-2007084647 A2 * | 7/2007 ........... A61B 5/4547 |
| WO | WO-2009146164 A1 | 12/2009 |
| WO | WO-2010001401 A1 | 1/2010 |
| WO | WO-2012011101 A2 | 1/2012 |

OTHER PUBLICATIONS

Institution Decision, *3Shape A/S v. Align Technology, Inc.*, IPR2019-00134, Paper No. 8, (P.T.A.B. Jul. 22, 2019).

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

(56) References Cited

OTHER PUBLICATIONS

Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 5000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chapuis, et al. A New System for Computer-Aided Preoperative Planning and Intraoperative Navigation During Corrective Jaw Surgery. IEEE Trans Inf Technol Biomed May 2007; 11(3):274-87.
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of

(56) References Cited

OTHER PUBLICATIONS

Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 page 1998).

International search report and written opinion dated Apr. 11, 2014 for PCT/IL2011/000574.

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy as One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http:// www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, a Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

(56) References Cited

OTHER PUBLICATIONS

Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.

Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Appliances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).

* cited by examiner

METHODS AND SYSTEMS FOR CREATING AND INTERACTING WITH THREE DIMENSIONAL VIRTUAL MODELS

CROSS REFERENCE

This application is a continuation of U.S. patent application Ser. No. 15/050,673, filed Feb. 23, 2016, which is a continuation of U.S. patent application Ser. No. 13/574,723, filed Jan. 4, 2013, now U.S. Pat. No. 9,299,192, issued Mar. 29, 2016, which is a U.S. National Phase Application under 35 U.S.C. § 371 of International Application No. PCT/IL11/00574, filed Jul. 19, 2011, which claims priority to U.S. Provisional Patent Application No. 61/365,556, filed Jul. 19, 2010, the entire contents of which are incorporated herein by reference.

FIELD OF THE INVENTION

This invention relates to methods and systems that are useful in dentistry and other fields and that are particularly useful in prosthodontics and/or orthodontics.

BACKGROUND OF THE INVENTION

There are many procedures associated with the intra oral cavity in which a precise three-dimensional virtual representation of the intra oral cavity can be useful to the dental practitioner.

Such virtual representations (also referred to interchangeably herein as "virtual models", "computer models", "3D numerical entities", and so on) enable the practitioner to study the intra oral cavity of individual patients via a computer system, in a similar manner to the study of the traditional physical plaster model. Furthermore, three-dimensional numerical entities of the intra oral cavity also allow the practitioner to study methods or approaches when dealing with particular dental problems of any given patient, and for the design of physical entities, for example prostheses, dental brackets, aligners and so on, in relation therewith. For example, in prosthodontics, a computer model of a patient's teeth may be manipulated to provide machining data to manufacture a physical model of the intra oral cavity, and/or to design and manufacture a coping and/or a prosthesis, while in orthodontics a computer model of a patient's teeth may be manipulated to enable a dental appliance, including for example orthodontic brackets and/or aligners, to be designed and manufactured, and/or for designing a treatment.

A parameter used in the design and manufacture of a dental prosthesis, such as a crown or bridge, is the finish line, or transition boundary between the prosthesis and the dental preparation, and this needs to be precisely defined in three-dimensions. Obtaining finish line coordinates from a computer virtual model is more efficient and often more accurate than from a plaster cast, and moreover facilitates the production of such a prosthesis, for example via CNC machining, rapid prototyping, or other computerized technologies, if desired.

However, it is often the case that when scanning the intra oral cavity to obtain 3D data of the preparation and finish line, on which the virtual model is based, part of the finish line, and possibly also the shoulder and other parts of the preparation, may be obscured by soft tissues such as the gum that, no longer being supported by the dental surfaces that have been removed, deform to cover at least a part of the finish line on the prepared dental site.

Additionally or alternatively, part or all of the finish line may be obscured by other agents or materials, including, for example, accumulation of one or more of saliva, blood, lubricant used with a dental drill, debris resulting from working the dental site, and so on.

Similar issues may arise when scanning the intra oral cavity to obtain 3D data of the position and orientation of a dental implant in relation to the surrounding portions of the intra-oral cavity, and in addition the corresponding impression abutment (also referred to herein as a scanning body) may partially obscure part of the intra-oral cavity.

Similarly, there are other situations in which a virtual model of a physical item, obtained from scanning the physical item, is partially obscured or incomplete, or in which part of the physical item needs to be subsequently modified after obtaining the virtual model. Such situations would conventionally require a rescanning of the entire physical item, and this may involve significant additional time, inconvenience and, where the physical item is a part of the body of a patient (such as for example the intra oral cavity), this may also involve significant patient discomfort.

SUMMARY OF THE INVENTION

Herein "intra oral cavity" (also referred to interchangeably herein as dental cavity) is taken to include, but not be limited to, one or more real teeth and/or one or more prosthetic teeth and/or part of one or more real teeth, of one jaw or of both jaws of a patient, and/or can also include all the real teeth and/or prosthetic teeth in one or both jaws, and/or adjacent gingiva and other adjacent objects of the patient, and/or can include a physical model or other physical representation of one or more or all the real teeth, and/or one or more or all of the prosthetic teeth, and/or part of one or more or all the real teeth, of one jaw or of both jaws, and/or of adjacent gingiva and/or other adjacent objects, of the patient.

Herein, "dental material" refers to any material associated with dental structures of the intra oral cavity, including but not limited to natural dental materials such as for example enamel, dentine, pulp, dental roots, and also including non-natural dental materials from which items such as for example metallic and non-metallic fillings, restorations, crowns, bridges, copings, preparations, and so on, are made from.

Herein, "dental clinic" refers to the interface between a dental practitioner and a patent, and thus includes any physical entity, in particular a clinic, in which there is interaction between a dental patient and a dental practitioner. While "dental practitioner" typically refers to a dentist, doctor or dental technician, it also includes herein all other caregivers, including for example dental surgeons, orthodontists, prosthodontists, dental assistants or any other caregiver or professional that may interact with a dental patient during the course of a dental treatment, or that may be involved in determining, preparing or providing dental treatment to a patient, particularly prosthodontic treatment and/or orthodontic treatment. While "dental patient" (also referred to interchangeably herein as "patient") typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, or veneering, or any other artificial partial or complete denture.

The term "virtual", applied herein with respect to models, manipulation of models, and so on, in particular 3D virtual models, for example, refers to being created, simulated, manipulated, carried out, and so on by means of a CAD/CAM system, a computer, a computer network, or the like, i.e., in a computer environment, particularly with reference to digital dentistry.

While the term "preparation" typically refers to the stump and including the finish line and shoulder that is left of the tooth that is to be replaced by the prosthesis—typically a crown—and on which the crown or other prosthesis is to be mounted or seated, the term "preparation" herein also includes artificial stumps, pivots, cores and posts, or other devices that may be implanted in the intraoral cavity in such a position or in a position that is optimal for implanting the crown or other prosthesis.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "3D virtual model" is used herein synonymously with digital model, virtual model, 3D virtual model, 3D model, three dimensional model, 3D numerical entity, numerical entity, computer model, 3D computer model, dimensional data, 3D digitized data, 3D representation, and other such terms, and relates to a virtual representation in a computer environment of a real object, such as for example a dentition or at least a part of the intraoral cavity, or of a real (physical) model thereof, for example of a plaster model or a stone model of the dentition or any dental structure. In particular a virtual dental model is one example of such a 3D virtual model of a dental structure.

The term "physical part" is used herein, synonymously with "real part" to refer to a physical object, in particular a physical dental object having a real (physical) surface and included but not limited to part or all of the dentition of the intraoral cavity including dies, a coping, a prosthesis, and so on, or to a physical dental model of part or all of the dentition of the intraoral cavity including dies, a coping, a prosthesis, and so on.

The term "scanning" and its analogues refer to any procedure directed at obtaining 3D topographic data of a surface, particularly of a dental surface, wherein to provide a 3D virtual model, and thus includes mechanical-based or other contact systems and methods, typically based on 3D probes for example, and/or any other noncontact systems and methods included but not limited to optical-based systems and methods and/or radiation-based systems and methods, including for example confocal-based systems and methods, for example as disclosed in WO 00/08415, the contents of which are incorporated herein in their entirety by reference, x-ray systems and methods including CT systems and methods, laser scanners, ultrasound scanners, and/or indeed any other suitable system and method for providing 3D virtual model.

The terms "tool" and "machining tool" are taken herein interchangeably to include any tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by computer systems or other automated means.

According to a first aspect of the invention there is provided a computer based method for modifying a virtual model of a physical structure, comprising:
(A) displaying an image of said virtual model on a display operatively connected to a computer system;
(B) identifying at least a portion of said virtual model that is desired to be modified by interacting with the displayed image,
(C) modifying said virtual model by replacing in the computer system at least said portion of said virtual model with additional 3D data obtained from the physical structure to provide a modified virtual model.

For example, the physical structure can comprise any one of an intra-oral cavity of a patient and a physical dental model representative of said intra-oral cavity. Additionally or alternatively, said virtual model includes a first three dimensional (3D) virtual model representative of a first physical part of the physical structure, and step (A) comprises providing to the computer system said first 3D virtual model and displaying on said display a first display image corresponding to said first 3D virtual model.

For example, step (B) comprises identifying on said first display image at least a first display image portion thereof by interacting with said display, said first display image portion corresponding to said portion of said virtual model, and said portion of said virtual model being representative of a first physical portion of said first physical part, and optionally step (C) comprises, subsequent to step (B):
causing the computer system to at least one of delete, remove and replace said portion of said virtual model by applying a corresponding function, i.e., a corresponding computer-implemented function (i.e. a delete function, a remove function or a replace function, respectively) to said first display image portion via interaction with said first display image on said display, to provide a modified first 3D virtual model;
providing said additional 3D data in the form of a second 3D virtual model representative of a second physical part of said physical structure, wherein a spatial disposition of said second physical part with respect to said first physical part is known or determinable;
virtually registering said second 3D virtual model with respect to said modified first 3D virtual model to provide said modified virtual model wherein said portion of said virtual model is replaced with a corresponding part of said second 3D virtual model representative of a second physical portion of said second physical part;
outputting said modified virtual model from said computer system.

Alternatively, steps (B) and (C) comprise:
providing said additional 3D data in the form of a second 3D virtual model representative of a second physical part of said physical structure, wherein a spatial disposition of said second physical part with respect to said first physical part is known or determinable;
virtually registering said second 3D virtual model with respect to said first 3D virtual model and further displaying in said display a second display image corresponding to said second 3D virtual model in registry with said first 3D virtual model;
identifying on said first display image at least a first display image portion thereof by interacting with said display, said first display image portion corresponding to said portion of said virtual model, and said portion of said virtual model being representative of a first physical portion of said first physical part;

causing the computer system to at least one of delete, remove and replace said portion of said virtual model by applying a corresponding function, i.e., a corresponding computer-implemented function, i.e., a corresponding computer-implemented function (i.e. a delete function, a remove function or a replace function, respectively) to said first display image portion via interaction with said first display image on said display, to provide said modified virtual model, wherein said portion of said virtual model is replaced with a corresponding part of said second 3D virtual model representative of a second physical portion of said second physical part;

outputting said modified virtual model from said computer system.

For example, said first display image is visually encoded in a different manner to said second display image to facilitate identifying said first display image portion.

Additionally or alternatively, said second physical part at least partially overlaps said first physical portion of said first physical part of said physical structure to provide data on said spatial disposition of said second physical part with respect to said first physical part.

Additionally or alternatively, said second physical portion of said second physical part spatially corresponds to but is topographically different from said first physical portion of said first physical part.

Additionally or alternatively, said corresponding part of said second 3D virtual model spatially corresponds to but is topographically different from said portion of said virtual model.

Additionally or alternatively, said first virtual model part represents a corresponding said first physical part of the physical structure, wherein said first virtual model part is considered to fail to comply with a predetermined requirement therefor. For example, said predetermined requirement comprises providing high surface definition of a surface of interest in said first physical part of the physical structure. For example, at least a part of said surface of interest in said first portion of said first physical part was obscured when the said first 3D virtual model was created, and wherein said second portion of said second physical part corresponds to said first portion of said first physical part wherein said at least a part of said surface of interest is now unobscured. For example, said first portion of said first physical part was obscured with a material including one or more of saliva, debris, blood, and wherein said second portion of said second physical part corresponds to said first portion of said first physical part wherein said material has been removed from said surface of interest. For example, said first portion of said first physical part was obscured with an artifact, and wherein said second portion of said second physical part corresponds to said first portion of said first physical part wherein said artifact has been removed. For example, said artifact comprises an impression abutment or any other structure mounted onto a dental implant that is embedded in said physical structure.

Additionally or alternatively, said predetermined requirement comprises providing a surface of interest in said first physical part of the physical structure that is configured for enabling a prosthesis to be mounted with respect thereto. For example, at least a part of said surface of interest in said first portion of said first physical part is inadequate for enabling a prosthesis to be mounted with respect thereto, and wherein said second portion of said second physical part corresponds to said first portion of said first physical part wherein said at least a part of said surface of interest has been physically altered. For example, where said at least a part of said surface of interest has been physically altered via a material removal operation wherein to modify the topology of said at least a part of said surface of interest. An example of this is where said at least a part of said surface of interest comprises a finish line of a tooth onto which it is desired to mount the prosthesis, and said finish line is inadequately defined in said first portion of said first physical part, but where said finish line is adequately defined in said second portion of said second physical part.

For example, said at least part of said surface of interest comprises a preparation surface of a preparation of a tooth onto which it is desired to mount the prosthesis, wherein in said first portion of said first physical part said preparation surface is inadequate for mounting the prosthesis thereto, and wherein in said second portion of said second physical part said preparation surface is inadequate for mounting the prosthesis thereto.

Additionally or alternatively, said first virtual model part is distorted or deficient and fails to properly represent a corresponding said first physical part of the physical structure.

Additionally or alternatively, the method further comprises manufacturing a physical dental model of the intra oral cavity based on said modified virtual model.

Additionally or alternatively, the method further comprises designing an orthodontic treatment plan based on said modified virtual model.

Additionally or alternatively, the method further comprises manufacturing a dental aligner based on said modified virtual model.

Additionally or alternatively, the method further comprises manufacturing orthodontic appliances based on said modified virtual model.

Additionally or alternatively, the method further comprises manufacturing a dental prosthesis based on said modified virtual model.

According to the first aspect of the invention there is also provided a computer system configured for modifying a virtual model of a physical structure, comprising:

a display configured for displaying a display image of said virtual model and for identifying at least a portion of said virtual model that is desired to be modified responsive to interaction of a user with the displayed display image, and further configured for modifying said virtual model by replacing in the computer system at least said identified portion of said virtual model with additional 3D data obtained from the physical structure to provide a modified virtual model.

For example, the computer system can configured for applying a computer implemented method as defined above for the first aspect of the invention, mutatis mutandis.

According to the first aspect of the invention there is also provided a computer readable medium that embodies in a tangible manner a program executable for:

(A) enabling displaying a display image of a virtual model of a physical structure;

(B) enabling interaction with the displayed display image to identify at least a portion of said virtual model that is desired to be modified (C) enabling modifying said virtual model by replacing at least said identified portion of said virtual model with additional 3D data obtained from the physical structure to provide a modified virtual model.

For example, the program can be configured for applying a computer implemented method as defined above for the first aspect of the invention, mutatis mutandis. Additionally or alternatively, the computer readable medium comprises any one of optical discs, magnetic discs, magnetic tapes, or solid state memory storage.

According to a second aspect of the invention there is provided a computer based method for modifying a virtual model of a physical structure, comprising:

(A) providing to the computer system said virtual model obtained from the physical structure;

(B) providing to the computer system additional 3D data obtained from at least a part of the physical structure;

(C) identifying at least one portion of the virtual model that is desired to be modified with at least a part of said additional 3D data; and (D) modifying the virtual model in the computer system at least by replacing said at least one identified portion of said virtual model with said at least part of said 3D data to provide a modified virtual model.

For example, step (A) comprises displaying a display image of said virtual model on a display operatively connected to a computer system. For example, step (B) comprises displaying a display image of said modified virtual model on said display. For example, step (C) comprises identifying said at least one portion of the virtual model on said display. For example, step (C) comprises interacting with said display images on said display to thereby replace said corresponding portion of said virtual model with said portion of said additional 3D data.

Additionally or alternatively, said additional 3D data includes at least one portion thereof that corresponds to but is different from a corresponding portion of said virtual model.

For example, said physical structure comprises any one of an intra-oral cavity of a patient and a physical dental model representative of said intra-oral cavity.

Additionally or alternatively, said virtual model includes a first three dimensional (3D) virtual model representative of a first physical part of the physical structure, and step (A) comprises providing to the computer system said first 3D virtual model and displaying on said display a first display image corresponding to said first 3D virtual model. For example, the method can comprise identifying on said first display image at least a first display image portion thereof by interacting with said display, said first display image portion corresponding to said portion of said virtual model, and said portion of said virtual model being representative of a first physical portion of said first physical part.

For example, step (C) comprises:

causing the computer system to at least one of delete, remove and replace said portion of said virtual model by applying a corresponding function, i.e., a corresponding computer-implemented function (i.e. a delete function, a remove function or a replace function, respectively) to said first display image portion via interaction with said first display image on said display, to provide a modified first 3D virtual model;

providing said additional 3D data in the form of a second 3D virtual model representative of a second physical part of said physical structure, wherein a spatial disposition of said second physical part with respect to said first physical part is known or determinable;

virtually registering said second 3D virtual model with respect to said modified first 3D virtual model to provide said modified virtual model wherein said portion of said virtual model is replaced with a corresponding part of said second 3D virtual model representative of a second physical portion of said outputting said modified virtual model from said computer system.

For example, steps (B) and (C) comprise:

providing said additional 3D data in the form of a second 3D virtual model representative of a second physical part of said physical structure, wherein a spatial disposition of said second physical part with respect to said first physical part is known or determinable;

virtually registering said second 3D virtual model with respect to said first 3D virtual model and further displaying in said display a second display image corresponding to said second 3D virtual model in registry with said first 3D virtual model;

identifying on said first display image at least a first display image portion thereof by interacting with said display, said first display image portion corresponding to said portion of said virtual model, and said portion of said virtual model being representative of a first physical portion of said first physical part;

causing the computer system to at least one of delete, remove and replace said portion of said virtual model by applying a corresponding function (i.e. a delete function, a remove function or a replace function, respectively) to said first display image portion via interaction with said first display image on said display, to provide said modified virtual model, wherein said portion of said virtual model is replaced with a corresponding part of said second 3D virtual model representative of a second physical portion of said second physical part;

outputting said modified virtual model from said computer system.

For example, said first display image is visually encoded in a different manner to said second display image to facilitate identifying said first display image portion.

Additionally or alternatively, said second physical part at least partially overlaps said first physical portion of said first physical part of said physical structure to provide data on said spatial disposition of said second physical part with respect to said first physical part.

Additionally or alternatively, said second physical portion of said second physical part spatially corresponds to but is topographically different from said first physical portion of said first physical part.

Additionally or alternatively, corresponding part of said second 3D virtual model spatially corresponds to but is topographically different from said portion of said virtual model.

Additionally or alternatively, said first virtual model part represents a corresponding said first physical part of the physical structure, wherein said first virtual model part is considered to fail to comply with a predetermined requirement therefor. For example, said predetermined requirement comprises providing high surface definition of a surface of interest in said first physical part of the physical structure. For example, at least a part of said surface of interest in said first portion of said first physical part was obscured when the said first 3D virtual model was created, and wherein said second portion of said second physical part corresponds to said first portion of said first physical part wherein said at least a part of said surface of interest is now unobscured. For example, said first portion of said first physical part was obscured with a material including one or more of saliva, debris, blood, and wherein said second portion of said second physical part corresponds to said first portion of said first physical part wherein said material has been removed from said surface of interest. For example, said first portion of said first physical part was obscured with an artifact, and wherein said second portion of said second physical part corresponds to said first portion of said first physical part wherein said artifact has been removed. For example, said artifact comprises an impression abutment or any other structure mounted onto a dental implant that is embedded in said physical structure.

Additionally or alternatively, said predetermined requirement comprises providing a surface of interest in said first physical part of the physical structure that is configured for enabling a prosthesis to be mounted with respect thereto. For example, at least a part of said surface of interest in said first portion of said first physical part is inadequate for enabling a prosthesis to be mounted with respect thereto, and wherein said second portion of said second physical part corresponds to said first portion of said first physical part wherein said at least a part of said surface of interest has been physically altered. For example, where said at least a part of said surface of interest has been physically altered via a material removal operation wherein to modify the topology of said at least a part of said surface of interest. An example of this is where said at least a part of said surface of interest comprises a finish line of a tooth onto which it is desired to mount the prosthesis, and said finish line is inadequately defined in said first portion of said first physical part, but where said finish line is adequately defined in said second portion of said second physical part.

For example, said at least a part of said surface of interest comprises a preparation surface of a preparation of a tooth onto which it is desired to mount the prosthesis, wherein in said first portion of said first physical part said preparation surface is inadequate for mounting the prosthesis thereto, and wherein in said second portion of said second physical part said preparation surface is inadequate for mounting the prosthesis thereto.

Additionally or alternatively, said first virtual model part is distorted or deficient and fails to properly represent a corresponding said first physical part of the physical structure.

Additionally or alternatively, the method further comprises manufacturing a physical dental model of the intra oral cavity based on said modified virtual model.

Additionally or alternatively, the method further comprises designing an orthodontic treatment plan based on said modified virtual model.

Additionally or alternatively, the method further comprises manufacturing a dental aligner based on said modified virtual model.

Additionally or alternatively, the method further comprises manufacturing orthodontic appliances based on said modified virtual model.

Additionally or alternatively, the method further comprises manufacturing a dental prosthesis based on said modified virtual model.

According to the second aspect of the invention there is also provided a computer system configured for modifying a virtual model of a physical structure, the system:
  (A) configured for enabling said virtual model obtained from the physical structure to be provided thereto;
  (B) configured for enabling additional 3D data obtained from at least a part of the physical structure to be provided thereto;
  (C) configured for enabling identifying at least one portion of the virtual model that is desired to be modified with at least a part of said additional 3D data;
  (D) configured for modifying the virtual model at least by replacing said corresponding portion of said virtual model with said portion of said additional 3D data to provide a modified virtual model.

For example, the computer system comprises a display operatively connected to the computer system, and the computer system can configured for applying a computer implemented method as defined above for the second aspect of the invention, mutatis mutandis.

According to the second aspect of the invention there is also provided a computer readable medium that embodies in a tangible manner a program executable for:
  (A) enabling a virtual model obtained from the physical structure to be provided thereto;
  (B) enabling additional 3D data obtained from at least a part of the physical structure to be provided thereto;
  (C) enabling identifying at least one portion of the virtual model that is desired to be modified with at least a part of said additional 3D data;
  (D) enabling modifying the virtual model at least by replacing said corresponding portion of said virtual model with said portion of said additional 3D data to provide a modified virtual model.

For example, the program can be configured for applying a computer implemented method as defined above for the second aspect of the invention, mutatis mutandis. Additionally or alternatively, the computer readable medium comprises any one of optical discs, magnetic discs, magnetic tapes, or solid state memory storage.

According to a third aspect of the invention there is provided a computer based method for modifying a virtual model of a physical structure, comprising:
  (A) providing to the computer system said virtual model obtained from the physical structure;
  (B) providing to the computer system additional 3D data obtained from the physical structure, said additional 3D data including at least one portion thereof that corresponds to but is different from a corresponding portion of said virtual model;
  (C) modifying the virtual model in the computer system at least by replacing said corresponding portion of said virtual model with said portion of said additional 3D data to provide a modified virtual model.

For example, step (A) comprises displaying a display image of said virtual model on a display operatively connected to a computer system For example, step (B) comprises identifying said corresponding portion of said virtual model on said display.

Additionally or alternatively step (C) comprises interacting with said display image on said display to thereby replace said corresponding portion of said virtual model with said portion of said additional 3D data.

Additionally or alternatively said physical structure comprises any one of an intra-oral cavity of a patient and a physical dental model representative of said intra-oral cavity.

Additionally or alternatively said virtual model includes a first three dimensional (3D) virtual model representative of a first physical part of the physical structure, and step (A) comprises providing to the computer system said first 3D virtual model and displaying on said display a first display image corresponding to said first 3D virtual model. For example, the method comprises identifying on said first display image at least a first display image portion thereof by interacting with said display, said first display image portion corresponding to said portion of said virtual model, and said portion of said virtual model being representative of a first physical portion of said first physical part.

For example, step (C) comprises:

causing the computer system to at least one of delete, remove and replace said portion of said virtual model by applying a corresponding function, i.e., a corresponding computer-implemented function (i.e. a delete function, a remove function or a replace function, respectively) to said first display image portion via interaction with said first display image on said display, to provide a modified first 3D virtual model;

providing said additional 3D data in the form of a second 3D virtual model representative of a second physical part of said physical structure, wherein a spatial disposition of said second physical part with respect to said first physical part is known or determinable;

virtually registering said second 3D virtual model with respect to said modified first 3D virtual model to provide said modified virtual model wherein said portion of said virtual model is replaced with a corresponding part of said second 3D virtual model representative of a second physical portion of said second physical part;

outputting said modified virtual model from said computer system.

For example, steps (B) and (C) comprise:

providing said additional 3D data in the form of a second 3D virtual model representative of a second physical part of said physical structure, wherein a spatial disposition of said second physical part with respect to said first physical part is known or determinable;

virtually registering said second 3D virtual model with respect to said first 3D virtual model and further displaying in said display a second display image corresponding to said second 3D virtual model in registry with said first 3D virtual model;

identifying on said first display image at least a first display image portion thereof by interacting with said display, said first display image portion corresponding to said portion of said virtual model, and said portion of said virtual model being representative of a first physical portion of said first physical part;

causing the computer system to at least one of delete, remove and replace said portion of said virtual model by applying a corresponding function, i.e., a corresponding computer-implemented function (i.e. a delete function, a remove function or a replace function, respectively) to said first display image portion via interaction with said first display image on said display, to provide said modified virtual model, wherein said portion of said virtual model is replaced with a corresponding part of said second 3D virtual model representative of a second physical portion of said second physical part;

outputting said modified virtual model from said computer system.

For example, said first display image is visually encoded in a different manner to said second display image to facilitate identifying said first display image portion.

Additionally or alternatively, said second physical part at least partially overlaps said first physical portion of said first physical part of said physical structure to provide data on said spatial disposition of said second physical part with respect to said first physical part.

Additionally or alternatively, said second physical portion of said second physical part spatially corresponds to but is topographically different from said first physical portion of said first physical part.

Additionally or alternatively, said corresponding part of said second 3D virtual model spatially corresponds to but is topographically different from said portion of said virtual model.

Additionally or alternatively, said first virtual model part represents a corresponding said first physical part of the physical structure, wherein said first virtual model part is considered to fail to comply with a predetermined requirement therefor.

For example, said predetermined requirement comprises providing high surface definition of a surface of interest in said first physical part of the physical structure. For example, at least a part of said surface of interest in said first portion of said first physical part was obscured when the said first 3D virtual model was created, and wherein said second portion of said second physical part corresponds to said first portion of said first physical part wherein said at least a part of said surface of interest is now unobscured. For example, said first portion of said first physical part was obscured with a material including one or more of saliva, debris, blood, and wherein said second portion of said second physical part corresponds to said first portion of said first physical part wherein said material has been removed from said surface of interest. For example, said first portion of said first physical part was obscured with an artifact, and wherein said second portion of said second physical part corresponds to said first portion of said first physical part wherein said artifact has been removed. For example, said artifact comprises an impression abutment or any other structure mounted onto a dental implant that is embedded in said physical structure.

For example, said predetermined requirement comprises providing a surface of interest in said first physical part of the physical structure that is configured for enabling a prosthesis to be mounted with respect thereto. For example, at least a part of said surface of interest in said first portion of said first physical part is inadequate for enabling a prosthesis to be mounted with respect thereto, and wherein said second portion of said second physical part corresponds to said first portion of said first physical part wherein said at least a part of said surface of interest has been physically altered. For example, where said at least a part of said surface of interest has been physically altered via a material removal operation wherein to modify the topology of said at least a part of said surface of interest. An example of this is where said at least a part of said surface of interest comprises a finish line of a tooth onto which it is desired to mount the prosthesis, and said finish line is inadequately defined in said first portion of said first physical part, but where said finish line is adequately defined in said second portion of said second physical part.

For example, said at least a part of said surface of interest comprises a preparation surface of a preparation of a tooth onto which it is desired to mount the prosthesis, wherein in said first portion of said first physical part said preparation surface is inadequate for mounting the prosthesis thereto, and wherein in said second portion of said second physical part said preparation surface is inadequate for mounting the prosthesis thereto.

Additionally or alternatively, said first virtual model part is distorted or deficient and fails to properly represent a corresponding said first physical part of the physical structure.

Additionally or alternatively, the method further comprises manufacturing a physical dental model of the intra oral cavity based on said modified virtual model.

Additionally or alternatively, the method further comprises designing an orthodontic treatment plan based on said modified virtual model.

Additionally or alternatively, the method further comprises manufacturing a dental aligner based on said modified virtual model.

Additionally or alternatively, the method further comprises manufacturing orthodontic appliances based on said modified virtual model.

Additionally or alternatively, the method further comprises manufacturing a dental prosthesis based on said modified virtual model.

According to the third aspect of the invention there is also provided a computer system configured for modifying a virtual model of a physical structure, the system being:

(A) configured for enabling said virtual model obtained from the physical structure to be provided thereto;

(B) configured for enabling additional 3D data obtained from the physical structure to be provided thereto, said additional 3D data including at least one portion thereof that corresponds to but is different from a corresponding portion of said virtual model;

(C) configured for modifying the virtual model at least by replacing said corresponding portion of said virtual model with said portion of said additional 3D data to provide a modified virtual model.

For example, the computer system comprises a display operatively connected to the computer system, and the computer system can configured for applying a computer implemented method as defined above for the third aspect of the invention, mutatis mutandis.

According to the third aspect of the invention there is also provided a computer readable medium that embodies in a tangible manner a program executable for:

(A) enabling said virtual model obtained from the physical structure to be provided thereto;

(B) enabling additional 3D data obtained from the physical structure to be provided thereto, said additional 3D data including at least one portion thereof that corresponds to but is different from a corresponding portion of said virtual model;

(C) modifying the virtual model at least by replacing said corresponding portion of said virtual model with said portion of said additional 3D data to provide a modified virtual model.

For example, the program can be configured for applying a computer implemented method as defined above for the third aspect of the invention, mutatis mutandis. Additionally or alternatively, the computer readable medium comprises any one of optical discs, magnetic discs, magnetic tapes, or solid state memory storage.

It is readily apparent that in at least some embodiment according to one or more of the first, second or third aspects of the invention, the second 3D virtual model contains new or additional 3D data of the first physical part of said physical structure in a region thereof corresponding to the first virtual model part that was deleted or removed or replaced. Said differently, the second 3D virtual model contains 3D data representative of a region of the first physical part of said physical structure having a spatial relationship with the rest of the first physical part corresponding to the virtual spatial relationship of first virtual model part of said first 3D virtual model (that was deleted or removed or replaced) with respect to the respective rest of the first 3D virtual model.

In at least some embodiments of the invention, said physical structure is a dental structure. For example, said physical structure comprises at least a part of an intra-oral cavity of a patient. For example, said physical structure comprises a physical dental model representative of at least a part of an intra-oral cavity of a patient. In other embodiments of the invention, the physical structure may be a non-dental structure.

It is readily apparent that in at least some embodiment according to one or more of the first, second or third aspects of the invention, the first 3D virtual model is analyzed by a user with respect to criteria to determine the suitability of the first physical part for the purpose of allowing a prosthesis to be seated thereon. While this analysis may be a visual and intuitive analysis by the user, the analysis may be optionally carried out by the computer system (or indeed by a different computer system) using suitable software, wherein the analysis may be fully automated or interactive with the user. The analysis may also be configured for identifying regions of the first physical part (i.e., on the first 3D virtual model) that require physical change—for example, the criteria may include the amount of original tooth reduction required at various points on the tooth to allow for good prosthesis seating and to allow for a minimum prosthetic thickness that is consistent with mechanical integrity standards therefor. The analysis software may further identify these regions and mark them automatically. Furthermore, the deleting/removing/replacing step can also be carried out automatically once these regions are marked, either immediately, or following a confirmation command from the user. Thereafter the user can rework the physical part, in particular the preparation in the regions thereof previously identified by the analysis software and now erased and missing in the modified first 3D virtual model.

Some specific embodiments according to at least one of the first, second or third aspect of the invention are provided below:

Embodiment A (a) A first virtual model (computer 3D model) VM1 of a physical part RM1 of the intra-oral cavity (typically of a patient, in vivo, but alternatively the scan may be of a physical dental model, or of an impression of the intra oral cavity, or of an impression a physical dental model) including tooth or teeth of interest is created, for example by scanning with an optical scanner, x-ray scanner, laser scanner or other scanner.

(b) Virtual model VM1 is displayed (and optionally magnified and/or manipulated) to visually check the model.

(c) A part DVMI of the virtual model is "deleted" (or otherwise removed) interactively on the screen by the user, resulting in a modified first virtual model VM1'.

(d) For example, this deleted part DVM1 of the model may not be acceptable and needs to be better defined for some dental procedure. The deleted part DVM1 may correspond, for example, to a part of a dental surface DRM1 that was not clearly defined in the first virtual model VM1 because, for example, during the initial scan that resulted in VM1, the corresponding part DRM1 of the physical dental surface was covered with saliva, blood, debris, or otherwise obscured by another element such as for example part of the gums, cheek, tongue, dental instruments etc.

(e) For example, the dental procedure may be providing a dental prosthesis, and the deleted part DVM1 may be part of the finish line that was not clear.

(f) A second virtual model VM2 is created, representing the part DRM1 of the physical dental surface plus additional identifying surface data ID.

(g) For example, the part DRM1 of the physical dental surface is cleaned up and/or unobstructed, and then rescanned. The scanning procedure also includes scanning an additional part P2 the real dental surface surrounding the part DRM1 to obtain additional identifying surface data ID.

(h) The second virtual model VM2 is then manipulated in the computer system to register it onto the modified first virtual model VM1'. In this connection, the identifying surface data ID of second virtual model VM2 may be useful as it may be aligned with corresponding parts of the modified first virtual model VM1', since the surface data for part P2 of the real physical dental surface should be nominally identical in both scans.

(j) In this aligned position, a part DVM2 of the second virtual model VM2 fits in and corresponds to the deleted portion DVM1, and part DVM2 is then stitched to modified first virtual model VM1' to create a further modified first virtual model VM1". The remainder of the second virtual model VM2, including the identifying surface data ID may then be discarded.

(k) The further modified first virtual model VM1" thus replaces the undesired part DVM1 of the original virtual model VM1 with new data.

(l) The above steps (b) to (k) may be repeated as often as desired.

A feature of at least this embodiment is that the user only needs to "correct" parts of the original virtual model of the dental surface, and does not need to rescan everything, should part of the virtual model not be acceptable.

Embodiment B (A) This is similar to Embodiment A, mutatis mutandis, the main difference being that the physical part RM1 of the intra-oral cavity includes a removable artifact which may be temporarily obscuring part of the dental surfaces.

(B) For example, the artifact may be a scanning body or impression abutment or any other structure that is mounted onto a dental implant and projects into the intra oral cavity so that the spatial orientation and other characteristics of the implant (which is already anchored in the jaw and thus cannot be seen) with respect to the dental surfaces may be derived from the position/orientation of the artifact. Alternatively, the artifact may be a prosthesis, such as a crown for example, that is mounted to the implant or that is temporarily seated onto a preparation.

(C) The first virtual scan thus includes the artifact and all the other dental areas of interest, but the presence of the artifact makes it difficult to obtain a full scan of the dental surface as the artifact may be too close in parts to the dental surfaces (e.g. an adjacent tooth).

(D) The part of the virtual model corresponding to the dental surface (and possibly also part of the artifact) is deleted or otherwise removed interactively in a similar manner to steps (b) and (c) above for Embodiment A, mutatis mutandis.

(E) The artifact is removed from the intraoral cavity and an area of the dental surfaces including the area that was not fully defined previously is scanned, and in the absence of the artifact, full definition should be achieved.

(F) The original virtual model in (A) for Embodiment B is then modified with the new scan data obtained in (E), in a manner similar to steps (f) to (j) above for Embodiment A, mutatis mutandis.

(G) If necessary, the artifact itself (or part thereof) may also be scanned separately to further modify the original virtual model, if part of the artifact was deleted in step (D).

A feature of at least this embodiment is that it allows obtaining a virtual model of the intra oral cavity including such an artifact, wherein even the parts of the dental surfaces originally obscured by the artifact can be fully defined with respect thereto.

Embodiment C (i) This is also similar to Embodiment A, mutatis mutandis, the main difference being that the physical part RM1 of the intra-oral cavity is well defined in the virtual model, but the physical part RM1 is not suitable for the dental procedure.

(ii) For example, the part RM1 may be a dental preparation for a dental prosthesis (e.g. a crown), and analysis of the first dental model with respect to a virtual model of the opposing dentition of the opposite jaw reveals that the form of the preparation would result in an inadequate structure for the prosthesis. For example, the dental preparation is too long, and would result in the thickness of the crown at the cusp being too thin and thus mechanically weak.

(iii) For example, a technique based on the virtual occlusion map invention, as disclosed in U.S. Pat. No. 6,334,853, assigned to Cadent Ltd, may be used for determining the distances between the preparation and the opposed dental surfaces, which provides a measure of the corresponding thickness of the respective dental prosthesis.

(iv) The part of the first virtual model that corresponds to the unsuitable part of the dental preparation is then deleted, as in step (c) above for Embodiment A, mutatis mutandis.

(v) The real dental preparation is also modified by the dental practitioner in the areas found to be unsuitable in (ii), and thereafter the preparation is scanned in the newly worked area, also including additional part of the preparation that was not altered.

(vi) The scan data corresponding to the unaltered area is used for aligning the new scan data for the worked part of the dental preparation in a similar manner to (h), (j), (k) above for Embodiment A, mutatis mutandis, to provide a modified virtual model.

(vii) The newly modified virtual model of (vi) is checked as in (ii) and (iii), and if necessary, steps (ii) to (vi) repeated as often as required, until the newly modified virtual model has a geometry for the dental preparation (corresponding to the real geometry of the dental preparation) that is adequate for a prosthesis.

In an alternative application of embodiment C in orthodontics, a patient's dentition is scanned and an orthodontic treatment is planned. Prior to commencing the treatment it is determined that the treatment may be improved by removing or filing some teeth. In such a case the areas including the removed/modified teeth are rescanned and these replace the parts of the original virtual model corresponding to these teeth. A new orthodontic treatment can then be planned based on the updated virtual model, and aligners and/or other orthodontic appliances can then be manufactured.

A feature of at least this embodiment is that it allows the dental practitioner to modify a dental structure (such as for example a dental preparation or a missing or modified tooth) in a quick and easy manner with a minimum of scanning after the initial virtual scan.

According to at least one aspect of the invention there is provided a system and method are provided for modifying a virtual model of a physical structure by displaying an image of the virtual model, deleting 3D data of parts of the virtual model by interacting with the displayed image, and replacing at least a portion of the deleted 3D data with new 3D data obtained from the physical structure to provide a modified virtual model.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
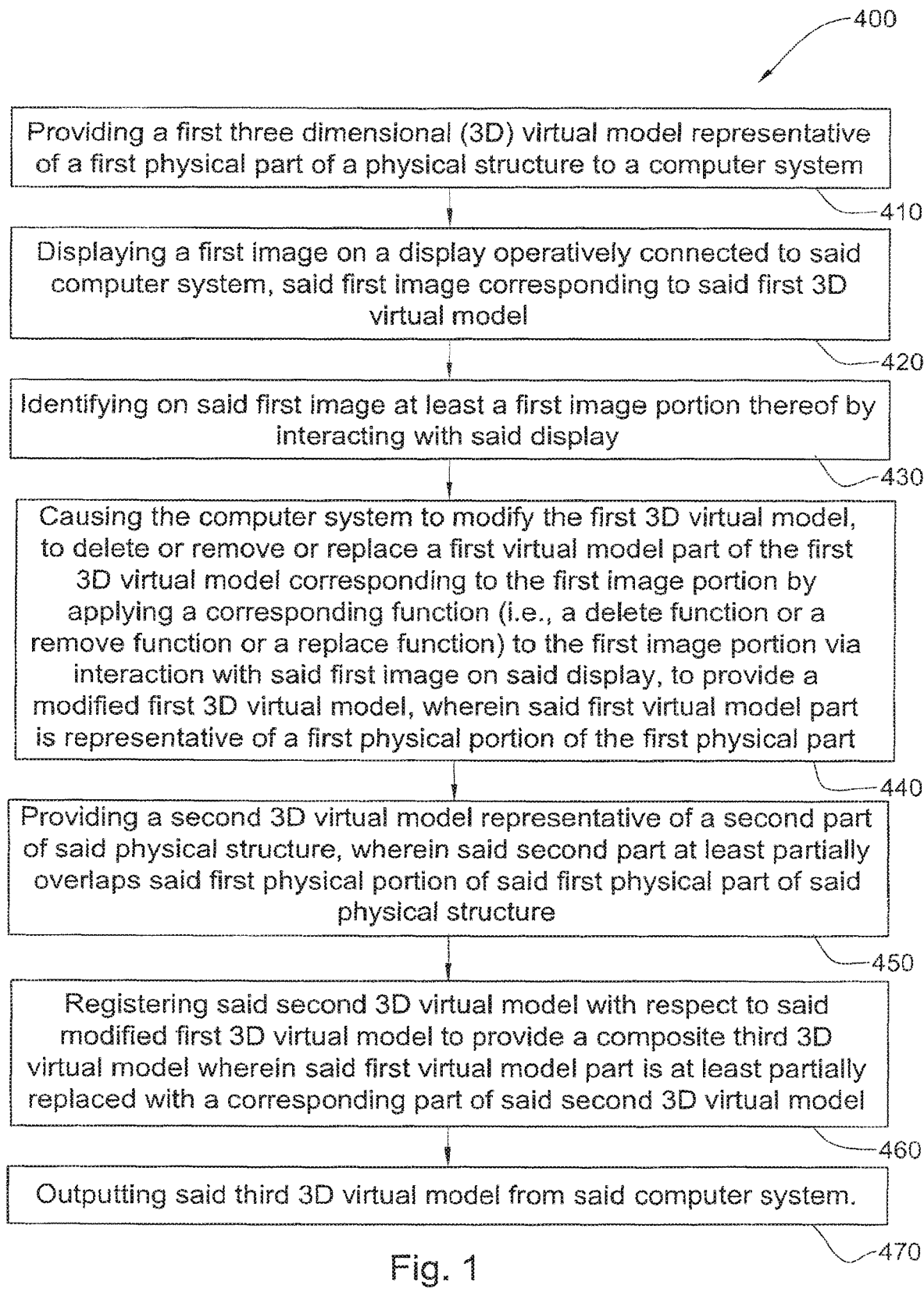
FIG. 1 shows, by way of a flow chart, a method m accordance with a first embodiment of the invention.

A computer-based method, particularly useful for creating, manipulating and refining a virtual dental model, according to a first embodiment of the invention and designated with reference numeral 400 is illustrated in FIG. 1.

In step 410 carried out by the method 400, an accurate 3D representation, i.e., a first 3D virtual model of a physical structure, in this example the intraoral cavity, is obtained. This first 3D virtual model is generally designated with the numeral VM1 in the accompanying figures. As used herein, and as already discussed, the intra oral cavity can include one or more real teeth and/or one or more prosthetic teeth and/or part of one or more real teeth of one jaw or of both jaws of a patient, and/or can also include all the real teeth and/or prosthetic teeth in one or both jaws, and/or adjacent gingiva and other adjacent objects of the patient, and/or can include a physical model or other physical representation of one or more or all the real teeth, and/or one or more or all of the prosthetic teeth, and/or part of one or more or all the real teeth, of one jaw or of both jaws, and/or of adjacent gingiva and/or other adjacent objects, of the patient.

Figure 3:
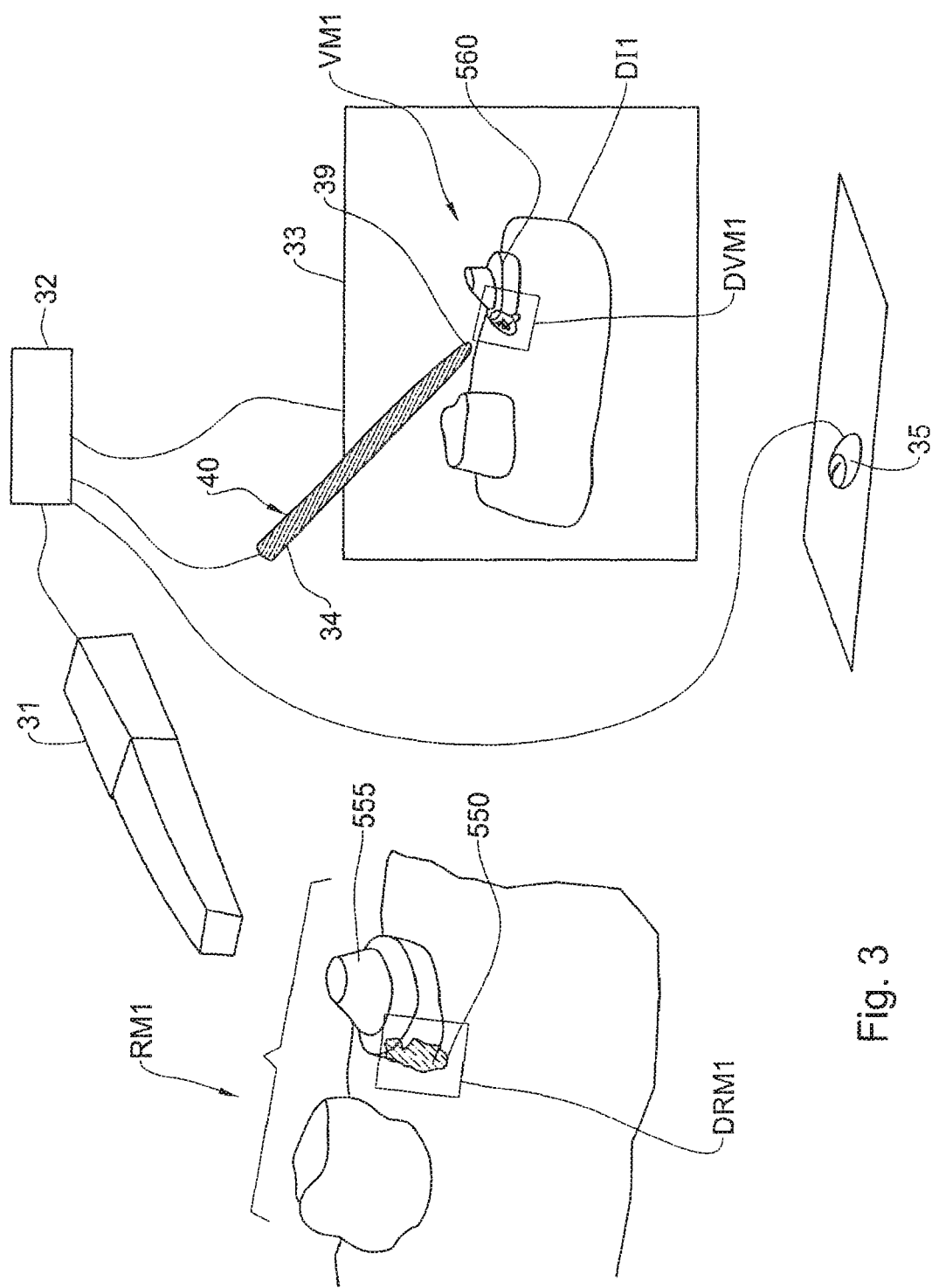
FIG. 3 schematically illustrates providing a first virtual model to the computer system of FIG. 2, and interacting with the display thereof.

Referring also to FIG. 3, the first 3D virtual model VM1 is thus representative of a physical part RM1 of the intra-oral cavity (typically of a patient, in vivo, but alternatively the first 3D virtual model VM1 may be of a physical dental model, as will become clearer below) including a tooth or teeth of interest.

Figure 2:
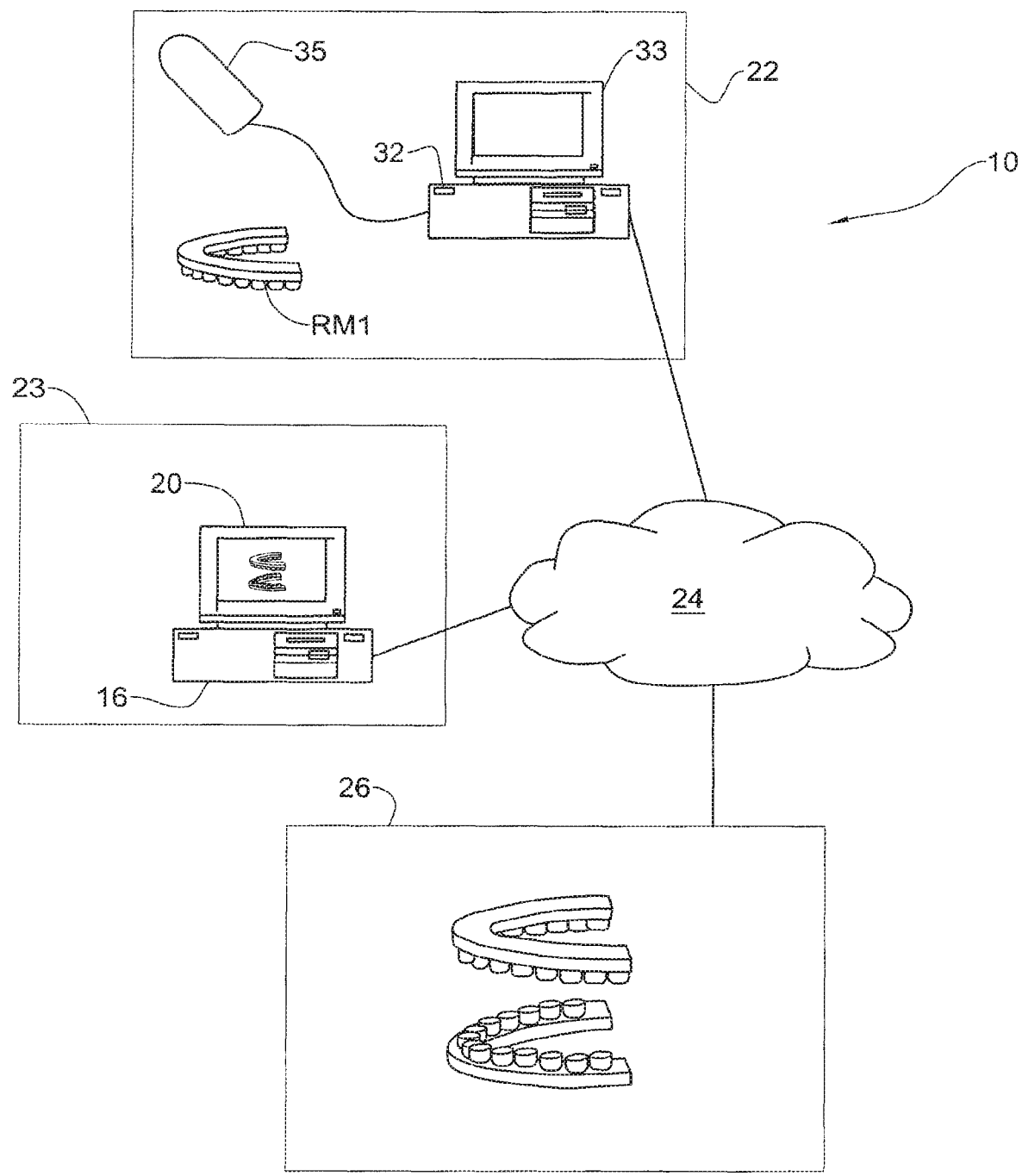
FIG. 2 shows various elements of a system used for providing and manipulating a virtual dental model according to the embodiment of FIG. 1.

The first 3D virtual model VM1, i.e. the 3D digitized data of the intraoral cavity, including the dentition and associated anatomical structures of a patient, may be provided using any suitable scanning equipment for scanning a patient's teeth, for example by scanning the intra oral cavity of the patient in vivo, or via scanning of a physical model or an impression thereof. Referring to FIG. 2, this may be done for example at a dental clinic 22 by the dentist or another dental practitioner. The dental clinic 22 is typically linked to one or more dental labs 26, and possibly also to a dental service center 23 via a communication means or network such as for example the Internet or other suitable communications medium such as an intranet, local access network, public switched telephone network, cable network, satellite communication system, and the like, indicated by the cloud at 24. The dental lab 26 is particularly adapted for defining the finish line, as well as for other tasks such as designing prostheses, designing and manufacturing physical models of the dentition, and possibly also for manufacturing at least an external profile of the prostheses. The dental service center 23 is particularly adapted for manufacturing dental hardware that requires a very high degree of precision, for example inner surfaces of prostheses that are required to match external surfaces of copings, and possibly also the copings themselves.

Such scanning equipment may include any suitable scanner, for example, an optical hand-held scanner 31 (or any other suitable optical scanner, mechanical scanner, ultrasound scanner, radiation-based scanner, including for example x-ray scanner, or other laser scanner, or any other suitable scanner) that is used by the practitioner to acquire the 3D data for example by directly scanning the patient's oral cavity. For example, a hand held apparatus including a probe for determining three dimensional structure by confocal focusing of an array of light beams can be used, for example as manufactured under the name of CB-CAD or as disclosed in WO 00/08415, the contents of which are incorporated herein by reference in their entirety, and in which in at least one embodiment, the apparatus is configured for determining surface topology of a portion of a three-dimensional structure, such as the intra oral cavity for example, the apparatus comprising:

a probing member with a sensing face;
an illumination unit for providing an array of incident light beams transmitted towards the structure along an optical path through said probing unit to generate illuminated spots on said portion;
a light focusing optics defining one or more focal planes forward said probing face at a position changeable by said optics, each light beam having its focus on one of said one or more focal plane;
a translation mechanism for displacing said focal plane relative to the structure along an axis defined by the propagation of the incident light beams;

a detector having an array of sensing elements for measuring intensity of each of a plurality of light beams returning from said spots propagating through an optical path opposite to that of the incident light beams;

a processor coupled to said detector for determining for each light beam a spot-specific position, being the position of the respective focal plane of said one or more focal planes yielding maximum measured intensity of the returned light beam, and based on the determined spot-specific positions, generating data representative of the topology of said portion.

The 3D data obtained by the scanner 31 may then be stored in a suitable storage medium, for example a memory in a computer workstation or system 32, which includes a display 33, such as for example a computer screen, operatively connected thereto. Typically, the 3D data can be sent over a suitable communication network 24 to the dental lab 26, for further processing. Optionally, the 3D data may be sent via communication network 24 to the dental service center 23, for the further processing.

The computer system 32 is configured for enabling the user to interact with images displayed in the display 33, and comprises an input device 40 configured for enabling the user to point to displayed objects on the display, and/or to interact with the display 33 to at least enable deletion and/or replacement of images thereon, as will become clearer below. The input device 40 may comprise, for example, a wand 34 (for example a light sensitive wand, or light pen) and/or a mouse 35, and/or the display 33 may incorporate the input device, being configured as a touch sensitive screen configured for at least enabling deletion and/or replacement of images thereon wherever a displayed image on the screen is touched or stroked by the user.

Optionally, color data of the intraoral cavity may also be provided together with the 3D data, and thus the virtual model comprises coordinates and corresponding color information of the dental surfaces scanned. Examples of such scanners are disclosed in co-pending application entitled "METHOD AND APPARATUS FOR COLOUR IMAGING A THREE-DIMENSIONAL STRUCTURE", published under US 2006-0001739, and which is assigned to the present Assignee. The contents of the aforesaid co-pending application are incorporated herein by reference in their entirety, and at least one embodiment of such a scanner comprises a device configured for determining the surface topology and associated color of at least a portion of a three dimensional structure, such as the intra oral cavity for example, comprising:

(a) scanning means adapted for providing depth data of said portion corresponding to a two-dimensional reference array substantially orthogonal to a depth direction;

(b) imaging means adapted for providing two-dimensional color image data of said portion associated with said reference array; wherein the device is adapted for maintaining a spatial disposition with respect to said portion that is substantially fixed during operation of said scanning means and said imaging means.

Such scanning means (a) may comprise the at least one embodiment of the apparatus disclosed in disclosed in WO 00/08415 and for example as defined above in connection therewith.

Alternatively or additionally, the clinic 22 may include equipment for obtaining a negative casting of a patient's teeth. In this case, the negative cast or impression can be taken of the patient's teeth, in a manner known in the art, and this physical negative model is dispatched to one of the dental labs 26 that is equipped to prepare from the negative model a physical positive cast suitable for scanning. The positive cast may be scanned at the dental lab 26 by any method known in the art, including for example x-ray scanning, laser scanning or using the aforesaid probe manufactured under the name of CB-CAD or as disclosed in WO 00/08415 and referred to above. The 3D data is then transmitted over the network 24 to the service center 23. Alternatively, the positive cast may be dispatched to the service center 23 by the dental clinic 22 and scanned at the service center 23 to obtain the 3D data. Alternatively, the service center 23 produces a positive model from the negative model and is scanned thereat, or sent to the dental clinic 22 to be scanned thereat. Alternatively, the negative model is scanned, either at the dental lab 26 or at the service center 23.

Alternatively, the negative model provided by the clinic 22 is sent to the service center 23, either directly by the clinic 22, or indirectly via the dental lab 26, and a composite physical positive-negative model may be manufactured from the original negative model. Thereafter, the positive-negative model may be processed to obtain 3D digitized data, for example as disclosed in U.S. Pat. No. 6,099,314, assigned to the present Assignee, and the contents of which are incorporated herein in their entirety.

Alternatively, the 3D first virtual model VM1 may be obtained in any other suitable manner, including other suitable intra oral scanning techniques, based on optical methods, direct contact or any other means, applied directly to the patient's dentition. Alternatively, X-ray based, CT based, MM based, or any other type of scanning of the patient or of a positive and/or negative model of the intra-oral cavity may be used. As is clear from the aforegoing, the dimensional data of the respective virtual model may be associated with a complete dentition, or of a partial dentition, for example such as a preparation only of the intra oral cavity.

Once the 3D digitized data is obtained, the virtual model VM1 is input to suitable computer system 32, and the next steps 420 to 470, are performed with the aid of computer system 32. In alternative variations of this embodiment, the scanner 31 provides raw data to the computer system 32 which then generates the first virtual model VM1 therein from this raw data.

In step 420, the first virtual model VM1 is displayed (and optionally magnified and/or manipulated) in display 33 as a first display image DI1 corresponding to the first virtual model VM1.

For example, the display 33 can be a 2D display such as conventional 2D display screen, and thus the images are 2D images. Alternatively, the display can be a 3D display and the images are also 3D images. Alternatively, the display can be a 2D stereoscopic display and the images are also 2D stereoscopic images.

The first virtual model VM1 can then be checked visually by the user via the image DI1 on the display 33. This image DI1 can be virtually manipulated on the display 33 with respect to up to six degrees of freedom (i.e., translated and/or rotated with respect to one or more of three mutually orthogonal axes) by suitably manipulating the first virtual model VM1 within the computer environment of system 32, using suitable user controls (hardware and/or virtual) to enable viewing the first virtual model VM1 from any desired direction on the screen 33 via the corresponding display image DI1 on the display 33, enabling the first virtual model VM1 to be visually checked by the user.

According to this embodiment, steps 430 to 470 are implemented when part of the first virtual model VM1, designated DVM1, is considered to be unsuitable or undesired, while concurrently it is desired to retain another part of the first virtual model VM1.

For example, this part DVM1 of the first virtual model VM1 may be considered by the user as not acceptable or desirable and needing to be better defined for a particular dental procedure of interest. The part DVM1 can correspond, for example, to a part of a real dental surface DRM1 of the real (physical) part RM1 of the intra-oral cavity that was not sufficiently clearly defined in the first virtual model VM1. For example, during the initial 3D data collection step, for example via scanning, that resulted in the first virtual model VM1 being generated, the corresponding part DRM1 of the physical dental surface was covered with foreign material, such as for example saliva, blood, debris, or was otherwise obscured by another element such as for example part of the gums, cheek, tongue, dental instruments, artifacts, etc. Alternatively, for example, during the initial 3D data collection step, for example via scanning, that resulted in the first virtual model VM1 being generated, the virtual part DVM1 may be distorted or otherwise defective and does not properly correspond to real part DRM1, for example due to some defect in the actual scanning process, while the real part DRM1 itself is acceptable.

In step 430 this part DVM1 of the first virtual model VM1 is marked on the first image of the first virtual model VM1 on the display 33. By "marked" it is meant that this zone or area of the first image DI1 is at least identified by the user, and may optionally include interacting with the display 33 so that a visual mark is included in the image to show and demarcate this area on the image DI1 that is on the display 33. For example, wand 34, operatively connected to the computer system 32 can be used for interacting with the display 33, wherein a visual mark is displayed wherever the tip 39 of the wand 34 touches the image DI1 on the display 33.

Figure 4:
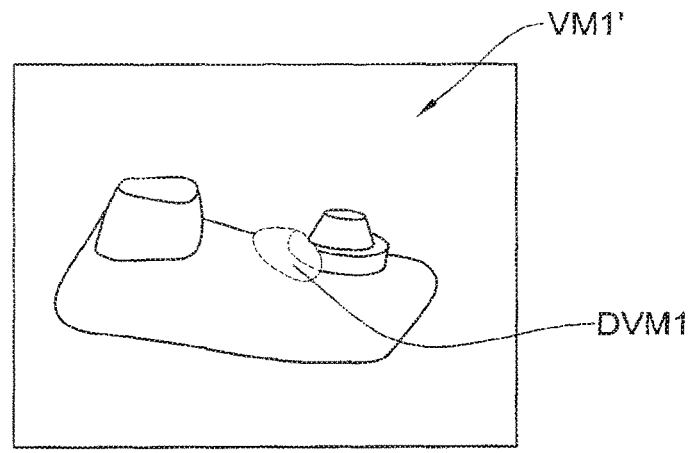
FIG. 4 schematically illustrated a modified first computer model as displayed by the computer system of FIG. 2.

In step 440, and referring also to FIG. 4, part DVM1 of the first virtual model VM1 is then "deleted" or otherwise removed or replaced interactively on the display 33 by the user, resulting in the first virtual model VM1 being modified to become a modified first virtual model VM1', by passing the tip of the wand 34 over the marked area of the image DI1. The deletion, removal or replacement of part DVM1 is responsive to the application of a special corresponding computer-implemented function (i.e. a corresponding deletion function, removal function or replacement function) via the computer system 32. The special computer-implemented function is, for ease of reference referred to herein as the "delete" function (and includes at least one of a remove function, remove command, delete command, replace command, or replace function) of the computer system 32, and operates to modify for example the first virtual model VM1 by at least one of deleting, removing or replacing a part thereof when "delete" function is activated, i.e., when the "delete" function is applied to the marked area of the image DI1.

According to this special "delete" function, the computer system 32 is configured for causing at least the deletion and/or removal and/or replacement of data corresponding to part DVM1 of the first virtual model VM1, when a corresponding part of the display image DI1 on the display 33 is correspondingly deleted or removed or replaced on the display 33, which in turn is accomplished by interaction by the user, such as touching the desired parts of the image DI1 on the display 33 with the wand 34 when the "delete" function is activated.

Although in at least one embodiment the display image DI1 is a two dimensional image, each element or pixel of such a 2D display image DI1 corresponds to a unique part of the three-dimensional data of the first virtual model VM1, as viewed in a viewing direction corresponding to image DI1, and thus the computer system is configured for deleting or removing or replacing such parts of the three-dimensional data from the first virtual model VM1 when the corresponding elements or pixels in the image DI1 are "touched" on the display 33 and the computer system 32 has the special "delete" function activated.

Particularly where the first virtual model VM1 represents a three dimensional surface of the physical part RM1, it is readily understood that the deleted or removed or replaced portions of the first virtual model VM1 are also three dimensional surfaces.

The above interaction for deletion or removal with respect to image DI1 can alternatively be accomplished without recourse to touching the display 33. For example, the computer system may be additionally or alternatively configured for enabling parts of the image DI1 to be deleted or removed by interaction therewith via mouse 35 or any other suitable input device 40.

The first virtual model VM1 is thus modified by the loss of the three dimensional data corresponding to part DVM1, effectively generating a modified first 3D virtual model VM1'.

For example, the dental procedure of interest may be providing a dental prosthesis, and the deleted or removed part DVM1 may be part of the finish line 550 of a preparation 555 that exists in real dental surface DRM1, but failed to be represented at all, or to be clearly represented, in the first virtual model VM1, for example due to obfuscation thereof by foreign material, distortion of the scanned data, etc, as discussed above, for example.

The dental surface DRM1 is thus considered the "first physical portion" of step 440.

Figure 5:
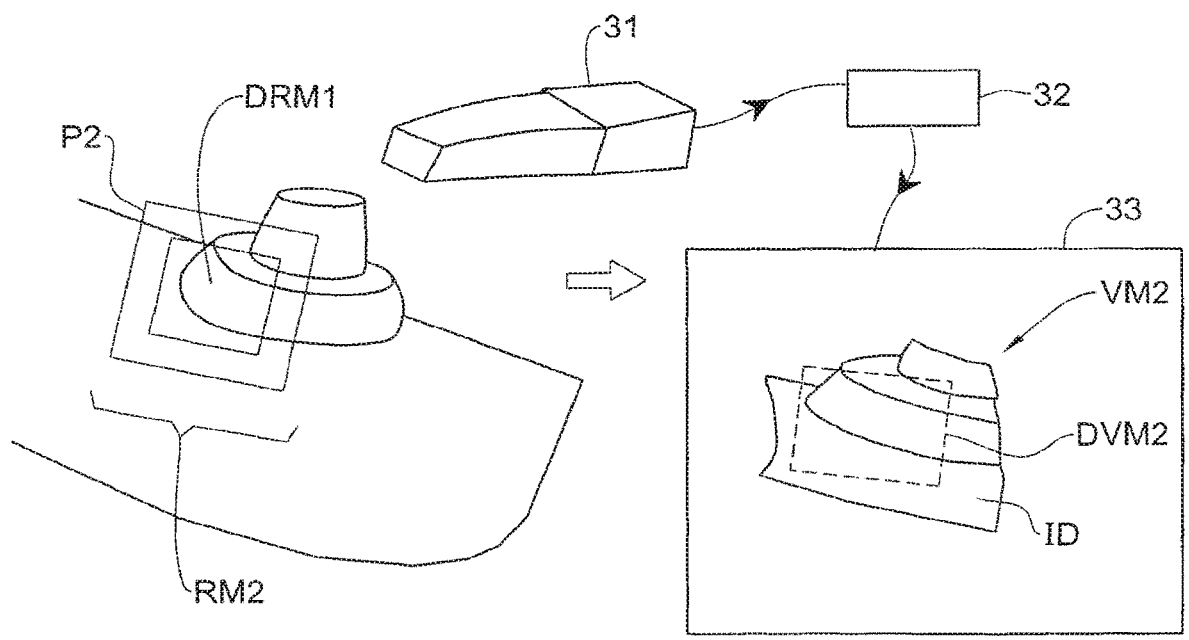
FIG. 5 schematically illustrates providing a second virtual model to the computer system of FIG. 2.

In step 450, and referring also to FIG. 5, a second virtual model VM2 is created, representing a second part RM2 of the physical dental structure. The second virtual model VM2 comprises a virtual part DVM2 that represents the part DRM1 of the physical dental surface, plus additional identifying surface data ID that represents a part P2 of the real dental surface in proximity to part DRM1, and thus second part RM2 at least partially overlaps with the physical part RM1. Before doing so, the part DRM1 of the physical dental surface is cleaned up and/or unobstructed, and for example rescanned to obtain second virtual model VM2. The scanning procedure thus also includes scanning the additional part P2 the real dental surface surrounding the part DRM1 to obtain additional identifying 3D surface data ID.

It is to be noted that in a variation of step 450, for example the virtual part DVM1 may be distorted or otherwise defective and does not properly correspond to real part DRM1, for example due to some defect in the actual scanning process thereof, while the real part DRM1 itself is acceptable. In such a case, second virtual model VM2 is created, representing a second part RM2 of the physical dental structure, and likewise the second virtual model VM2 comprises a virtual part DVM2 that represents the same part DRM1 of the physical dental surface, plus additional identifying surface data ID that represents a part P2 of the real dental surface in proximity to part DRM1, and thus second part RM2 at least partially overlaps with the physical part RM1. While scanning to provide the second virtual model VM2, it is now ensured that second virtual model VM2 is free from distortions or imperfections that originate from the scanning procedure itself.

Figure 6:
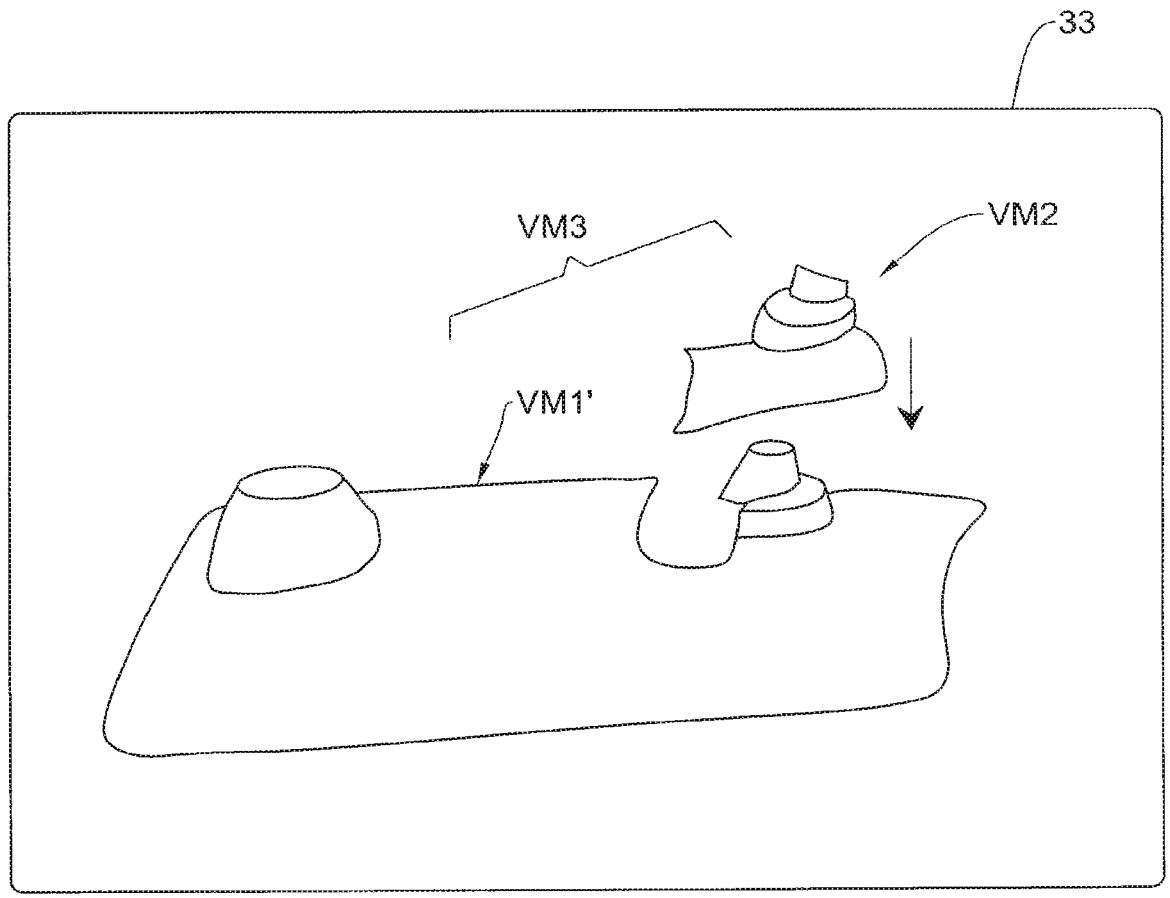
FIG. 6 schematically illustrates manipulating the second virtual model of FIG. 5 into registration with the modified computer model of FIG. 4.

In step 460, and referring also to FIG. 6, the second 3D virtual model VM2 is spatially registered with respect to the modified first 3D virtual model VM1' to provide a composite third 3D virtual model VM3, wherein the part DVM1 that was previously deleted/removed is at least partially replaced with a corresponding part the second 3D virtual model VM2. In particular, the second virtual model VM2 is manipulated in the computer system 32 to register the second virtual model VM2 onto the modified first virtual model VM1'. In this connection, the identifying surface data ID of second virtual model VM2 may be useful as it may be aligned with corresponding parts of the modified first virtual model VM1', since the surface data for part P2 of the real physical dental surface should be nominally identical in both scans. In this aligned position, part DVM2 of the second virtual model VM2 fits in and corresponds to at least a portion of the deleted portion DVM1, and part DVM2 is then stitched to modified first virtual model VM1' in a virtual manner to create a further modified first virtual model, i.e., composite third 3D virtual model VM3. The remainder of the second virtual model VM2, including the identifying surface data ID may then be discarded.

Alternatively, it may not be necessary that second part RM2 at least partially overlaps with the physical part RM1, and instead the 3D data defining each respective virtual model can be referred to the same global coordinate system in a different manner, for example via an optical marker whose 3D coordinates are known with respect to a global coordinate system, and which is scanned together with each one of second part RM2 and physical part RM1.

Thus, the composite third 3D virtual model VM3 replaces the undesired part DVM1 of the original virtual model VM1 with new 3D data provided by part DVM2.

It is readily evident that by carrying out steps 430 to 460, the user only needs to "correct" or modify parts of the original virtual model VM1 of the dental surface i.e. of physical part RM1, and does not need to obtain a new virtual model of the whole of physical part RM1 from scratch, should even a small part of the virtual model VM1 not be acceptable.

Figure 9:
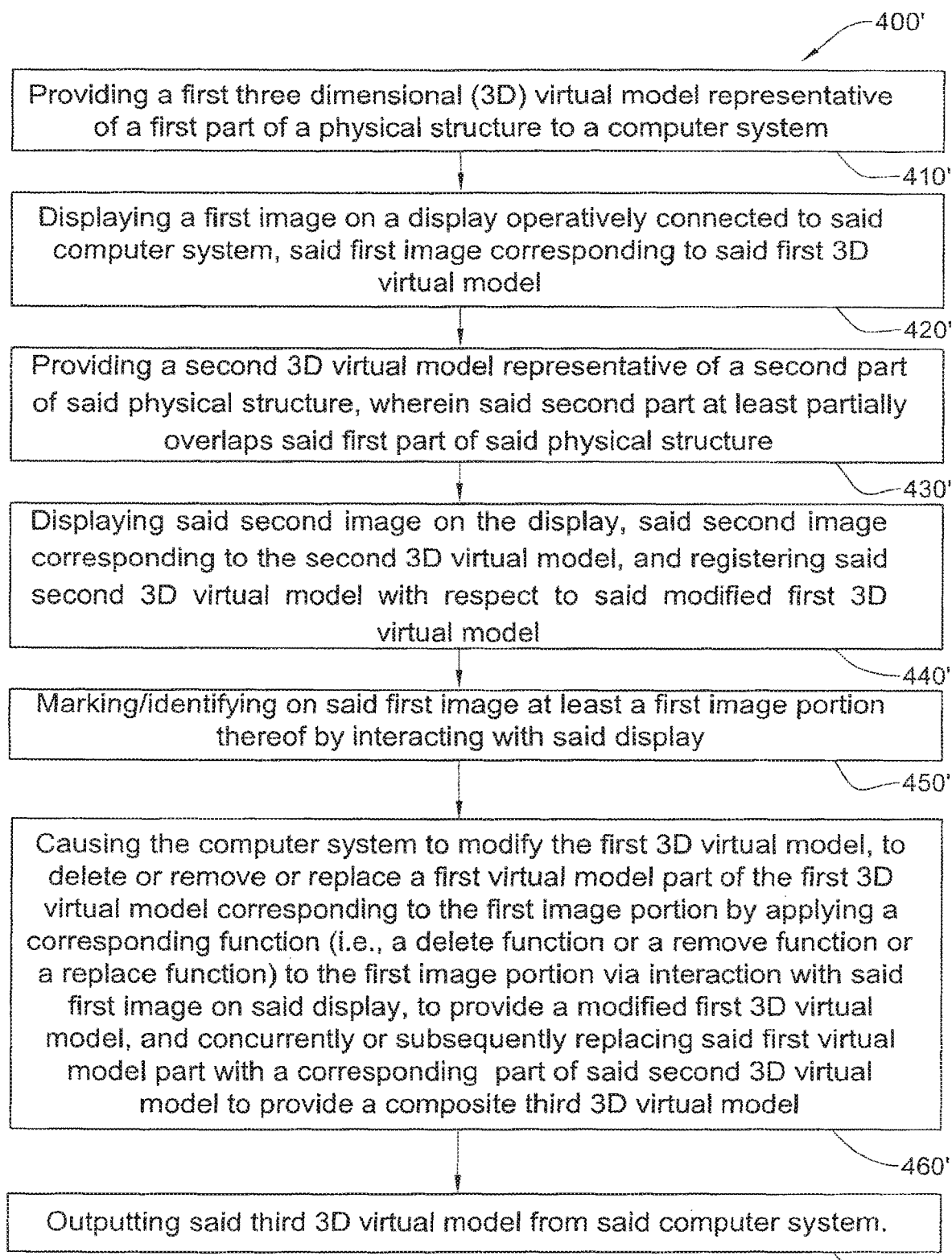
FIG. 9 shows, by way of a flow chart, a method in accordance with an alternative variation of the first embodiment of the invention.

In alternative variations of this embodiment, steps 430 to 460 may be implemented in a different manner. For example, and referring to FIG. 9, steps 430 to 460 may be replaced with steps 430' to 460' of modified method 400', which can include steps 410', 420' and 470' which are respectively identical to steps 410, 420, 470 of method 400 as disclosed herein, mutatis mutandis.

Step 430' comprises all the elements and features of step 450 as disclosed herein, mutatis mutandis, with the main difference that step 430' is implemented immediately following step 420'. In other words, and having carried out steps 410' and 420', the second virtual model VM2 is created, representing a second part RM2 of the physical dental structure. Again, the second virtual model VM2 comprises a virtual part DVM2 that represents the part DRM1 of the physical dental surface, plus additional identifying surface data ID that represents a part P2 of the real dental surface in proximity to part DRM1, and thus second part RM2 at least partially overlaps with the physical part RM1. Before doing so, the part DRM1 of the physical dental surface is cleaned up and/or unobstructed, and for example rescanned to obtain second virtual model VM2. The scanning procedure thus also includes scanning the additional part P2 the real dental surface surrounding the part DRM1 to obtain additional identifying 3D surface data ID.

Then, in step 440', second virtual model VM2 is virtually registered with the first virtual model VM1. In particular, the second virtual model VM2 is manipulated in the computer system 32 to register the second virtual model VM2 onto the first virtual model VM1. In this connection, the identifying surface data ID of second virtual model VM2 may be useful as it may be aligned with corresponding parts of the first virtual model VM1, since the surface data for part P2 of the real physical dental surface should be nominally identical in both scans. In this aligned position, part DVM2 of the second virtual model VM2, corresponds to, in particular spatially corresponds to, and is different from, in particular is topographically different from, at least a portion of the portion DVM1 of the first virtual model VM1 (as is the case also in steps 430 to 460 of method 400, mutatis mutandis). At this point, portion DVM1 has not yet been deleted, removed or identified.

In step 440', the second virtual model VM2 is also displayed (and optionally magnified and/or manipulated) in display 33 as a second display image DI2 corresponding to the second virtual model VM2, wherein display image DI2 is similar to first display image DI1 as disclosed herein, mutatis mutandis, but corresponds to the second virtual model VM2 rather than the first virtual model VM1. For example when using a 2D display, the second display image DI2 is also a two-dimensional image, but in 3D displays the second display image DI2 can be a 3D image as well, or in 2D stereoscopic displays the second display image DI2 can be a 2D stereoscopic image as well for example.

Both the second virtual model VM2 and the first virtual model VM1 are viewable on the display 33 via their respective images DI2 and DI1, either together in registry, or may be selectively viewed separately, in different display windows on the same display 33, for example, or alternately on the same display, or in different displays, and so on. To facilitate viewing the images in 3D registry, the images DI2 and DI1 may be visually encoded, each in a different manner. For example, the images DI2 and DI1 may be encoded each in a different color or shade of gray. Alternatively, at least parts of the images DI2 and DI1 which do not exactly correspond to one another may be color encoded in this manner to highlight the corresponding topographical differences between the real first part RM1 and the real second part RM2 of the physical dental structure.

In step 450', part DVM1 of the first virtual model VM1 is marked by the user on the first image of the first virtual model VM1 on the display 33, this part DVM1 having first been visually identified by the user from the images DI1 and DI2 displayed in step 440'. Thus, step 450' is similar to step 430 as disclosed herein, mutatis mutandis, and thus by "marked" it is meant that the user may optionally interact with this area of the first image DI1 in the display 33 so that a visual mark is included in the image to show and demarcate this area on the image DI1 that is on the display 33. For example, wand 34, operatively connected to the computer system 32 can be used for interacting with the display 33, wherein a visual mark is displayed wherever the tip 39 of the wand 34 touches the image DI1 on the display 33.

Step 460' is similar to step 440 as disclosed herein, mutatis mutandis, and thus part DVM1 of the first virtual model VM1 is then "deleted" or otherwise removed or replaced interactively on the display 33 by the user, resulting in the first virtual model VM1 being modified to become a modified first virtual model VM1', for example by passing the tip of the wand 34 over the marked area of the image DI1, when a special "delete" function (also referred to interchangeably herein as a remove function, remove command, or deleted command, or replace function, or replace command) of the computer system 32 is activated, i.e., when a corresponding function (delete function or remove function or replace function) is applied to the marked area of the image DI1. Step 460' in addition comprises part of step 460 as disclosed herein, mutatis mutandis, and, with the second 3D virtual model VM2 already registered with respect to the modified first 3D virtual model VM1 (step 440'), the part DVM1 that was previously deleted/removed is at least partially replaced with a corresponding part of the second 3D virtual model VM2. Alternatively, this function operates as a unified replacement function in which DVM1 is replaced in one operation with part DVM2.

In the aligned position of the registered modified first virtual model VM1' with second virtual model VM2, part DVM2 of the second virtual model VM2 virtually fits in and corresponds to at least a portion of the deleted portion DVM1, and part DVM2 is then stitched to modified first virtual model VM1' in a virtual manner to create a further modified first virtual model, i.e., composite third 3D virtual model VM3. The remainder of the second virtual model VM2, including the identifying surface data ID may then be discarded.

Thus, in step 470', a composite third 3D virtual model VM3 (comprising modified first virtual model VM1' part DVM2) effectively replaces the undesired part DVM1 of the original virtual model VM1 with new 3D data provided by part DVM2.

It is to be noted that at least in some alternative variations of the method 400', step 420' and/or step 440' can be omitted. For example, the user can scan the first physical part of the structure in step 410' and then without displaying the respective first 3D virtual model, proceed with scanning the second part of the physical structure in step 430' to provide the second 3D virtual model, also without displaying the respective second 3D virtual model. Thus, so long as the first 3D virtual model and the second 3D virtual model can be spatially registered (and thus the first physical part corresponds to (in particular spatially corresponds to) but may be different from (in particular topographically different from) the second physical part), step 460' can be implemented automatically and the first 3D virtual model replaces parts thereof with the second 3D virtual model, without the need to have these parts or the first 3D virtual model or the second 3D virtual model displayed, identified or marked. Such a situation may arise, for example, where the user suspects or knows (for example during or after scanning to provide the first 3D virtual model) that some portions of the scanned first part of the physical structure were for example obscured, ill-defined, badly scanned, and so on and need to be rescanned. The user can then go back to these portions of the physical structure and rescan those portions to provide the second 3D virtual model which then automatically replaces corresponding parts of the first 3D virtual model.

In a similar manner, mutatis mutandis, in at least in some alternative variations of the method 400, step 420 can be omitted, and steps 440 and 460 can be modified so that the interaction with the display is omitted, and the first 3D virtual model replaces parts thereof with the second 3D virtual model automatically via registration therewith, rather than implementing a delete function first, and a stitching function later.

Figure 7:
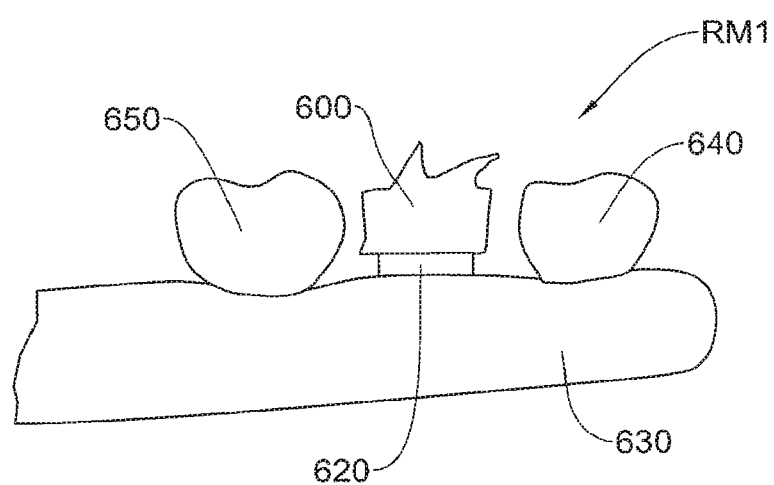
FIG. 7 schematically illustrates an example of physical part used in conjunction with a second embodiment of the invention.

Referring to FIG. 7, a second embodiment of the invention has all the elements, features and steps of the first embodiment including steps 410 to 470 or alternative variations thereof, for example steps 410' to 470', mutatis mutandis, the main difference being that in the second embodiment the physical part RM1 of the intra-oral cavity includes a removable physical artifact which may be temporarily obscuring part of the dental surfaces.

For example, the artifact may be a scanning body or impression abutment 600 (or any other structure) that is mounted onto a dental implant and projects into the intra oral cavity so that the spatial orientation and/or other characteristics of the implant 620 (which is already anchored in the jaw 630 and thus cannot be seen) with respect to the dental surfaces may be derived from the position/orientation of the artifact 600.

The first virtual model VM1 for this embodiment thus also includes a virtual representation of the artifact 600, as well as all the other dental areas of interest of the physical part RM1, but the presence of the artifact 600 may render it difficult or impossible to obtain at the same time a full scan of the physical part RM1, as the artifact 600 may be too close in parts to the dental surfaces (e.g. adjacent teeth 640, 650) and thus obscures or blocks the ability of a scanner to scan such areas.

In this embodiment, and in applying method 400 to this embodiment, in steps 420 and 430, each part of the virtual model corresponding to an obscured area (and possibly also corresponding to the artifact 600) is deleted interactively in a similar manner that disclosed above for the first embodiment, mutatis mutandis, to provide the corresponding modified first virtual model VM1'.

Then, and prior to step 440, the artifact 600, which is considered the "first physical portion" in step 440, is physically removed from the intraoral cavity and an area of the physical part RM1 including the previously obscured areas that were not fully defined previously in the first virtual model VM1 is scanned, in the absence of the artifact, enabling full definition of this area to be achieved in the corresponding second virtual model VM2 thereby generated.

Thereafter, in step 460, second virtual model VM2 is registered with the modified first virtual model VM1', in a manner similar to that disclosed above for the first embodiment, mutatis mutandis, to provide the corresponding the corresponding composite third virtual model VM3.

If necessary or desired, the artifact 600 itself (or part thereof) may also be scanned separately to obtain a virtual model thereof. This may be used to further modify the composite third virtual model, if for example part of the artifact was deleted in step 440.

Method 400' may be applied m a corresponding manner to the second embodiment, mutatis mutandis.

It is readily evident that by carrying out this embodiment of the invention, it allows obtaining a virtual model of the intra oral cavity including such an artifact, wherein even the parts of the dental surfaces obscured by the artifact can be fully defined with respect thereto, even when originally obscured by the artifact.

Figure 8:
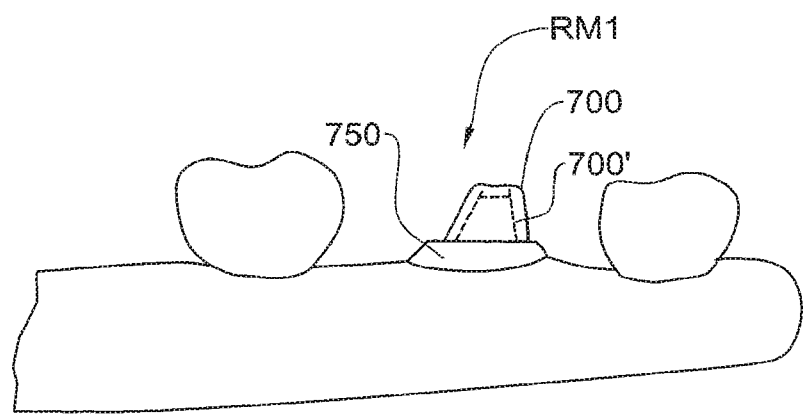
FIG. 8 schematically illustrates an example of physical part used in conjunction with a third embodiment of the invention.

Referring to FIG. 8, a third embodiment of the invention has all the elements, features and steps of the first embodiment including steps 410 to 470 or alternative variations thereof, for example steps 410' to 470', mutatis mutandis, the main difference being that the physical part RM1 in the third embodiment is considered to be well defined in the first virtual model VM1, i.e., faithfully represents the surfaces of interest of the physical part RM1; however, a first physical portion of the physical part RM1 is not considered suitable for a dental procedure.

For example, the physical part RM1 may be a dental preparation 700 for a dental prosthesis (e.g. a crown), and analysis of the first dental model with respect to a virtual model of the opposing dentition of the opposite jaw reveals that the form of the preparation would result in an inadequate structure for the prosthesis. For example, the dental preparation is too long and/or too thick, and would result in the thickness of the crown at the cusp being too thin, and thus mechanically weak.

In this connection, the distances between the preparation 700 and the opposed dental surfaces may be determined, for example, in a manner as disclosed in U.S. Pat. No. 6,334, 853, the contents of which are incorporated herein in their entirety, which in turn can provide a measure of the corresponding thickness of the respective dental prosthesis. In at least one embodiment disclosed in U.S. Pat. No. 6,334,853, there is provided a method for obtaining a dental occlusion map of a three-dimensional virtual computer model of teeth of upper and lower jaws of a mouth, said occlusion map indicative of distances between opposite regions on facing surfaces of opposite teeth of the upper and lower jaws of the mouth, said method comprising the steps of:

(i) determining said distances between opposite regions on opposite teeth of the upper and lower jaws of the mouth; and (ii) setting up a correspondence between said determined distances and regions on a mapping surface.

The part of the first 3D virtual model that corresponds to the unsuitable portion of the dental preparation 700 is then deleted or removed or replaced in steps 430 and 440 in applying method 400 to this embodiment, in a manner similar to that disclosed above for the first embodiment, mutatis mutandis.

The real dental preparation 700 is also physically modified by the dental practitioner in the areas found to be unsuitable for the prosthesis, for example via a material removal operation such as by using dental drills or dental lasers, for example, to provide a modified physical preparation 700'.

Thereafter, in step 450, a second virtual model VM2 corresponding to the modified preparation 700' is obtained, for example by scanning the newly worked area of the modified preparation 700', but also including additional part 750 of the preparation that was not altered in the material removal; process.

In step 460, second virtual model VM2 is registered with the modified first virtual model VM1', in a manner similar to that disclosed above for the first embodiment, mutatis mutandis, to provide the corresponding the corresponding composite third virtual model VM3.

A new cycle of checking and modifying the preparation can be initiated if desired or necessary, wherein the third virtual model previously generated can be considered to be a "first virtual model" for the new cycle, and checked as in step 420, mutatis mutandis, and if necessary, steps 430 to 460 repeated as often as required, each time providing a new third virtual model than can be considered, if desired as a new first virtual model, until the newly modified third virtual model has a geometry for the dental preparation (corresponding to the geometry of the real dental preparation) that is adequate for receiving a prosthesis, according to criteria.

It is also readily evident that rather than modifying the whole preparation, only part of the preparation, for example a part of the finish line, can be modified instead, and the method applied to this part only, saving considerable time by not having to scan the remainder of the preparation (that is considered acceptable) or surrounding areas, i.e., the whole physical part RM1 again each time.

Method 400' may be applied in a corresponding manner to the third embodiment, mutatis mutandis.

It is also readily evident that by carrying out this embodiment of the invention, it allows the dental practitioner to modify a dental structure such as dental preparation in a quick and easy manner with a minimum of scanning after the initial virtual scan. i.e., without the need to rescan the whole physical part RM1 again each time.

It also readily evident that parts or all of the method steps according to each of the first, second and third embodiments and/or alternative variations thereof may be applied to one or more of the other embodiments as well.

It is also readily evident that the method (and corresponding system) according to each of the first, second and third embodiments and/or alternative variations thereof may further comprise a manufacturing step, in which a dental object may be manufactured based on the respective composite third 3D virtual model VM3 under computer aided manufacture (CAM). Such a dental object may be manufactured, for example, based on a material removal operation that is performed by a computer aided removal operation machine having a suitable machining tool, using any suitable CAM (Computer Aided Manufacturing) technology, typically a CNC milling machine, on a blank of material. This material is typically plaster or any other type of material commonly used for dental models, however any other suitable material may be used. Alternatively, other CAM-based techniques may be used, for example rapid prototyping or any other suitable 3D printing technique, for creating the dental object. Accordingly, a dental object corresponding to composite third 3D virtual model VM3 or associated with the composite third 3D virtual model VM3 can be manufactured.

For example, the dental object may comprise a physical model of the intraoral cavity, and thus composite third 3D virtual model VM3 can be used directly to provide the necessary data for the CAM process.

In another example, and where the composite third 3D virtual model VM3 is based on one or more teeth requiring a prosthesis, and thus comprise a suitable preparation. A dental object in the form of the respective prosthesis may be prepared based on information from the composite third 3D virtual model VM3. The dentist or a technician may generate a 3D virtual prosthesis model of a crown to be fitted on a tooth stump (or of a bridge to be fitted on the tooth surface, or of any other prosthesis to be fitted to the tooth/teeth including any restoration and/or any onlays, and/or any inlays, such as caps, for example, or veneering, or any other artificial partial or complete denture), to generate a digital file. Alternatively, the outer surface of the prosthesis may be designed manually if desired. The prosthesis may then be manufactured using any suitable CAM techniques, for example as disclosed above, mutatis mutandis, and in a further step, the prosthesis may be installed in the oral cavity of the patient. Optionally, the virtual prosthesis model may also include a virtual model of a coping plus a virtual model of a cap that is to be mounted onto the coping. The coping may be manufactured using any suitable method, for example as disclosed in WO 2004/087000, also assigned to the present Assignee, and the contents of which are incorporated herein in their entirety. The cap or full prosthesis may be manufactured using any suitable method, for example as disclosed in U.S. Ser. No. 11/046,709 or in U.S. Provisional Application No. 60/632,350, also assigned to the present Assignee, and the contents of which are incorporated herein in their entirety.

In another example, and where the composite third 3D virtual model VM3 is based on one or more teeth requiring an orthodontic treatment, a set of aligners may be manufactured based on the composite third 3D virtual model VM3. For example, the teeth shown in the 3D virtual model, which normally would be of a patient's teeth in their initial positions, can be segmented (i.e. digitally cut into separate objects). The resultant digital data can then be used for orthodontic treatment planning. The individual teeth can be moved by a computer program and/or by an operator into a desired final setup. Then a number of digital intermediate tooth arrangements can be generated. These digital intermediate and final tooth arrangements of the treatment plan can be used to fabricate positive molds of intermediate arrangements (such as by using rapid proto typing equipment or milling machines) which are used to form aligners for moving teeth or they can be used to directly form aligners.

Alternatively, where the composite third 3D virtual model VM3 is based on one or more teeth requiring an orthodontic treatment, dental objects in the form of a set of orthodontic appliances, for example brackets, may be virtually designed and/or manufactured (for example using suitable CAM-based techniques) based on the composite third 3D virtual model VM3.

Furthermore, where the composite third 3D virtual model VM3 is based on one or more teeth requiring an orthodontic treatment, such an orthodontic treatment may be designed using a computer system based on third 3D virtual model VM3. For example such an orthodontic treatment may be provided by implementing a method for virtual orthodontic treatment, for example as disclosed in U.S. Pat. No. 6,739,869, also assigned to the present Assignee, and the contents of which are incorporated herein in their entirety, and at least one embodiment of such a method for virtual orthodontic treatment comprises:

(a) providing a first virtual three-dimensional (3D) image indicative of a 3D model of all teeth of at least one jaw, the model being manipulable so as to allow its viewing from a desired direction—for example such a first virtual three-dimensional (3D) image may be based on the composite third 3D virtual model VM3;

(b) selecting a virtual set of orthodontic components, comprising (i) brackets, one for each tooth in said first image, for attachment to teeth of said image, each of said brackets having a slot for engaging an arch wire, and (ii) one or two arch wires, one for each jaw of said first image;

(c) associating the brackets with the teeth of said first image so as to obtain a second image of said virtual 3D model with the brackets associated with the teeth of the model, one bracket on each teeth in said model; and (d) using a set of rules including a rule that requires each slot to engage the wire, computing the manner of movement of each tooth with the bracket associated therewith, so as to obtain a third image comprising the teeth model following the virtual treatment.

It is also readily evident that the method (and corresponding system) according to at least one embodiment of the present invention may be applied to obtaining a 3D virtual model of any physical structure, including non-dental structures, and in which it may be desired or necessary to re-scan a part of the structure, without the need to rescan the whole structure again to obtain an updated 3D virtual model of the physical structure. Such method (and corresponding system) may optionally be further used for manufacturing a physical object based on or associated with the updated 3D virtual model of the physical structure.

For example, the method (and corresponding system) according to at least one embodiment of the invention may be applied to scanning a complex circuit board comprising a plurality of chips mounted thereon, replacing one such ship and scanning the new chip in situ, and modifying the original 3D virtual model to replace the part thereof corresponding to the old chip with the 3D data corresponding to the new chip.

In another example, the method (and corresponding system) according to at least one embodiment of the invention may be applied to scanning a complex geometrical physical structure comprising a plurality of geometrical entities mounted or formed thereon, adding or removing a geometrical physical entity with respect to the structure, and scanning the modified physical structure in the area that includes the new geometrical entity or that includes the modification of the physical structure arising from the removal of the geometrical entity, respectively, and modifying the original 3D virtual model to replace a corresponding part thereof with the 3D data corresponding to the aforesaid scanned area.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed some embodiments in accordance with the invention, it will be appreciated that many changes may be made therein without departing from the spirit of the invention.

What is claimed is:

1. A dental system for intraorally scanning a patient's teeth for a dental procedure, the dental system comprising:
   a hand-held intraoral scanner; and
   a computer readable medium including instructions that when executed by a computer system, cause the computer system to:
   receive first 3D intraoral scan data of the patient's teeth from the hand-held intraoral scanner;
   display, to a display, a first 3D surface model of the patient's teeth, wherein the first 3D surface model of the patient's teeth is based on the received first 3D intraoral scan data of the patient's teeth;
   receive user input defining a surface portion of the first 3D surface model to be removed;
   after receiving the user input, remove, from the displayed first 3D surface model, the surface portion of the first 3D surface model to be removed according to the user input;
   after removing the surface portion of the first 3D surface model, receive second 3D intraoral scan data of the patient's teeth from the hand-held intraoral scanner, the second 3D intraoral scan data including surface data of a physically changed portion of the patient's intra-oral cavity;
   replace at least a portion of the removed surface portion of the first 3D surface model with at least a surface portion of a second 3D surface model including the physically changed portion based on the received second 3D intraoral scan data of the patient's teeth to produce a composite 3D surface model of the patient's teeth that is based on the first 3D intraoral scan data and the second 3D intraoral scan data; and
   output, to the display, the composite 3D surface model of the patient's teeth.

2. The system of claim 1, wherein the hand-held intraoral scanner comprises a probing member with a sensing face, an illumination unit, a light focusing optics defining one or more focal planes forward the sensing face, and a translation mechanism for displacing the one or more focal planes relative to the sensing face.

3. The system of claim 2, wherein the system further comprises the computer system and the display; wherein the system further comprises a mouse or wherein the display comprises a touch screen display; and wherein the user input defining portions of the first 3D surface model to be removed is received from the mouse or the touch screen display.

4. The system of claim 1, wherein the instructions to replace at least the portion of the removed surface portion of the first 3D surface model with at least the surface portion of the second 3D surface model includes instructions to register the second 3D surface model with the first 3D surface model.

5. The system of claim 4, wherein the second 3D surface model is registered with the first 3D surface model by aligning identifying surface data of the second 3D surface model with corresponding parts of the first 3D surface model.

6. The system of claim 5, wherein the instructions to replace at least the portion of the removed surface portion of the first 3D surface model with at least the surface portion of the second 3D surface model includes instructions to stitch the surface portion of the second 3D surface model with the first 3D surface model.

7. The system of claim 6, wherein the instructions to replace at least the portion of the removed surface portion of the first 3D surface model with at least the surface portion of the second 3D surface model includes instruction to discard a remainder of the second 3D surface model, including the identifying surface data, after stitching the surface portion of the second 3D surface model with the first 3D surface model.

8. The system of claim 1, wherein the computer readable medium further includes instructions that when executed by the computer system, cause the computer system to: mark, on the displayed first 3D surface model, the user input defined surface portion, after receiving the user input and before removing the surface portion.

9. A dental system for intraorally scanning a patient's teeth for a dental procedure, the dental system comprising:
a hand-held intraoral scanner;
a computer readable medium including instructions that when executed by a computer system, cause the computer system to:
receive first 3D intraoral scan data of the patient's teeth from the hand-held intraoral scanner;
display, to the display, a first 3D surface model of the patient's teeth, wherein the first 3D surface model of the patient's teeth is based on the received first 3D intraoral scan data of the patient's teeth;
receive user input via the displayed first 3D surface model demarcating a surface portion of the first 3D surface model to be retained and a surface portion of the first 3D surface model to be replaced;
after receiving the user input, receive second 3D intraoral scan data of the patient's teeth from the hand-held intraoral scanner, the second 3D intraoral scan data including surface data of a physically changed portion of the patient's intra-oral cavity;
replace at least a portion of the surface portion of the first 3D surface model to be replaced according to the user input with at least a surface portion of a second 3D surface model based on the received second 3D intraoral scan data of the patient's teeth that includes the physically changed portion while retaining the surface portion of the first 3D surface model to be retained according to the user input to produce a composite 3D surface model of the patient's teeth that is based on the first 3D intraoral scan data and the second 3D intraoral scan data; and
output, to the display, the composite 3D surface model of the patient's teeth.

10. The system of claim 9, wherein the hand-held intraoral scanner comprises a probing member with a sensing face, an illumination unit, a light focusing optics defining one or more focal planes forward the sensing face, and a translation mechanism for displacing the one or more focal planes relative to the sensing face.

11. The system of claim 9, wherein the computer readable medium further includes instructions that when executed by a computer system, cause the computer system to remove, from the displayed first 3D surface model, the surface portion of the first 3D surface model to be replaced according to the user input demarcating the surface portion of the first 3D surface model to be retained and the surface portion of the first 3D surface model to be replaced.

12. The system of claim 11, wherein the computer readable medium further includes instructions that when executed by the computer system, cause the computer system to: mark, on the displayed first 3D surface model, the user input defined surface portion to be replaced, after receiving the user input and before removing the surface portion to be replaced.

13. The system of claim 9, wherein the instructions to replace at least the portion of the surface portion of the first 3D surface model to be replaced with at least the surface portion of the second 3D surface model include instructions to register the second 3D surface model with the first 3D surface model by aligning identifying surface data of the second 3D surface model with corresponding parts of the first 3D surface model.

14. The system of claim 13, wherein the instructions to replace at least the portion of the surface portion of the first 3D surface model to be replaced with at least the surface portion of the second 3D surface model include instructions to stitch the surface portion of the second 3D surface model with the first 3D surface model.

15. The system of claim 14, wherein the instructions to replace at least the portion of the surface portion of the first 3D surface model to be replaced with at least the surface portion of the second 3D surface model include instructions to discard a remainder of the second 3D surface model, including the identifying surface data, after stitching the surface portion of the second 3D surface model with the first 3D surface model.

16. A dental system for intraorally scanning a patient's teeth for a dental procedure, the dental system comprising:
a hand-held intraoral scanner;
a display; and
a computer system operatively coupled with the display and the hand-held intraoral scanner, the computer system configured to:
receive first 3D intraoral scan data of the patient's teeth from the hand-held intraoral scanner;
display, to the display, a first 3D surface model of the patient's teeth, wherein the first 3D surface model of the patient's teeth is based on the received first 3D intraoral scan data of the patient's teeth;

receive user input via the displayed first 3D surface model at least defining a surface portion of the first 3D surface model to be retained;

after receiving the user input, receive second 3D intraoral scan data of the patient's teeth from the hand-held intraoral scanner, the second 3D intraoral scan data including surface data of a physically changed portion of the patient's intra-oral cavity;

replace at least a portion of the first 3D surface model not part of the surface portion of the first 3D surface model to be retained according to the user input with at least a surface portion of a second 3D surface model based on the received second 3D intraoral scan data of the patient's teeth that includes the physically changed portion to produce a composite 3D surface model of the patient's teeth that is based on the first 3D intraoral scan data and the second 3D intraoral scan data; and output, to the display, the composite 3D surface model of the patient's teeth.

17. The system of claim 16, wherein the hand-held intraoral scanner comprises a probing member with a sensing face, an illumination unit, a light focusing optics defining one or more focal planes forward the sensing face, and a translation mechanism for displacing the one or more focal planes relative to the sensing face.

18. The system of claim 16, wherein the received user input also defines a surface portion of the first 3D surface model to be replaced by the second 3D surface model.

19. The system of claim 18, wherein the computer system is further configured to remove, from the displayed first 3D surface model, the surface portion to be replaced according to the user input defining the surface portion of the first 3D surface model to be retained and the surface portion of the first 3D surface model to be replaced.

20. The system of claim 16, wherein at least the portion of the first 3D surface model not part of the surface portion of the first 3D surface model to be retained according to the user input is replaced with at least the surface portion of the second 3D surface model by registering the second 3D surface model with the first 3D surface model by aligning identifying surface data of the second 3D surface model with corresponding parts of the first 3D surface model.

21. The system of claim 20, wherein at least the portion of the first 3D surface model to be replaced is replaced with at least the surface portion of the second 3D surface model by further stitching the surface portion of the second 3D surface model with the first 3D surface model.

22. The system of claim 21, wherein at least the portion of the first 3D surface model to be replaced is replaced with at least the surface portion of the second 3D surface model by further discarding a remainder of the second 3D surface model, including the identifying surface data, after stitching the surface portion of the second 3D surface model with the first 3D surface model.

23. A dental method for intraorally scanning a patient's teeth for a dental procedure, the dental method comprising:
receiving first 3D intraoral scan data of the patient's teeth from a hand-held intraoral scanner;
displaying, to a display, a first 3D surface model of the patient's teeth, wherein the first 3D surface model of the patient's teeth is based on the received first 3D intraoral scan data of the patient's teeth;
receiving user input via the displayed first 3D surface model demarcating a surface portion of the first 3D surface model to be retained and a surface portion of the first 3D surface model to be replaced;
after receiving the user input, receiving second 3D intraoral scan data of the patient's teeth from the hand-held intraoral scanner, the second 3D intraoral scan data including surface data of a physically changed portion of the patient's intra-oral cavity;
replacing at least a portion of the surface portion of the first 3D surface model to be replaced according to the user input with at least a surface portion of a second 3D surface model based on the received second 3D intraoral scan data of the patient's teeth including the physically changed portion to produce a composite 3D surface model of the patient's teeth that is based on the first 3D intraoral scan data and the second 3D intraoral scan data; and
output, to the display, the composite 3D surface model of the patient's teeth.

24. The method of claim 23, further comprising marking an area, on the displayed first 3D surface model, associated with the received user input.

25. The method of claim 23, wherein replacing at least the portion of the surface portion of the first 3D surface model to be replaced according to the user input with at least the surface portion of the second 3D surface model comprises registering the second 3D surface model with the first 3D surface model by aligning identifying surface data of the second 3D surface model with corresponding parts of the first 3D surface model.

26. The method of claim 25, wherein replacing at least the portion of the surface portion of the first 3D surface model to be replaced according to the user input with at least the surface portion of the second 3D surface model further comprises stitching the surface portion of the second 3D surface model with the first 3D surface model.

27. The method of claim 26, wherein replacing at least the portion of the surface portion of the first 3D surface model to be replaced according to the user input with at least the surface portion of the second 3D surface model further comprises discarding a remainder of the second 3D surface model, including the identifying surface data, after stitching the surface portion of the second 3D surface model with the first 3D surface model.

28. The method of claim 23, wherein the first 3D surface model of the patient's teeth comprises a tooth preparation having a finish line, wherein a portion of the finish line is obscured or distorted, and wherein the physical change results in the finish line not being obscured or distorted.

29. The method of claim 23, wherein the first 3D surface model of the patient's teeth comprises a tooth preparation that accurately represents a surface of a physical preparation of the patient, and wherein the method further comprises analyzing the tooth preparation of the first 3D surface model to determine whether the surface of the physical preparation is suitable for a dental prosthesis; and wherein the physical change is a physical modification of the surface of the physical preparation of the patient.

30. The method of claim 29, wherein the dental prosthesis comprises a dental crown and wherein the tooth preparation analysis comprises analysis of the first 3D surface model with respect to a virtual model of an opposing dentition of an opposite jaw to determine whether the tooth preparation would result in an inadequate structure for the dental crown.

* * * * *